US010369288B2

(12) United States Patent
Okabe

(10) Patent No.: US 10,369,288 B2
(45) Date of Patent: Aug. 6, 2019

(54) SEALING CONTAINER

(71) Applicant: Norimoto Okabe, Tokyo (JP)

(72) Inventor: Norimoto Okabe, Tokyo (JP)

( * ) Notice: Subject to any disclaimer, the term of this patent is extended or adjusted under 35 U.S.C. 154(b) by 0 days.

(21) Appl. No.: 15/682,895

(22) Filed: Aug. 22, 2017

(65) Prior Publication Data

US 2017/0348490 A1 Dec. 7, 2017

Related U.S. Application Data

(63) Continuation of application No. PCT/JP2016/056318, filed on Mar. 1, 2016.

(30) Foreign Application Priority Data

Mar. 15, 2015 (JP) ................................ 2015-051527

(51) Int. Cl.
*A61M 5/28* (2006.01)
*B65D 51/22* (2006.01)
(Continued)

(52) U.S. Cl.
CPC ................ *A61M 5/28* (2013.01); *B65D 25/20* (2013.01); *B65D 25/42* (2013.01); *B65D 51/22* (2013.01);
(Continued)

(58) Field of Classification Search
CPC ...... A61M 5/28; A61M 5/285; A61M 5/1483; A61M 5/145; A61M 5/14248;
(Continued)

(56) References Cited

U.S. PATENT DOCUMENTS 3,964,641 A * 6/1976 Langensiepen ... B05C 17/00586
222/82
4,425,122 A * 1/1984 Cohen ..................... A61M 5/34
604/237
(Continued)

FOREIGN PATENT DOCUMENTS

DE 102010042740 A1 * 4/2012 ........... B05B 11/048
EP 1495775 A1 * 1/2005 ........ A61M 5/14248
(Continued)

*Primary Examiner* — Nathan R Price
*Assistant Examiner* — Mark Alan Igel
(74) *Attorney, Agent, or Firm* — Muramatsu & Associates

(57) ABSTRACT

A sealing container is designed to enable a user to adjust the timing of discharging the contents. The sealing container includes: a bag-shaped member for accommodating the contents therein, a sealing film for sealing the bag-shaped member, an opening means so configured that at least a part of which is movable toward the sealing film and is capable of opening the sealing film, an operation unit for performing an operation of moving the opening means, and a discharge means configured to be capable of discharging the contents from the bag-shaped member at a timing different from a timing at which the opening means penetrates the sealing film by operating the operation unit. It is possible for the user to perform only the operation of opening the sealing film by operating the operation unit, so that the user is able to arbitrarily adjust the timing at which the content is discharged from the bag-shaped member of the sealing container.

15 Claims, 20 Drawing Sheets

(51) Int. Cl.
| | |
|---|---|
| *B65D 73/00* | (2006.01) |
| *B65D 75/52* | (2006.01) |
| *B65D 77/40* | (2006.01) |
| *B65D 25/20* | (2006.01) |
| *B65D 25/42* | (2006.01) |
| *B65D 75/70* | (2006.01) |
| *B65D 75/32* | (2006.01) |
| *B65D 75/58* | (2006.01) |
| *B65D 77/06* | (2006.01) |
| *B65D 83/00* | (2006.01) |

(52) U.S. Cl.
 CPC ....... *B65D 51/226* (2013.01); *B65D 73/0078* (2013.01); *B65D 75/32* (2013.01); *B65D 75/52* (2013.01); *B65D 75/5877* (2013.01); *B65D 75/70* (2013.01); *B65D 77/068* (2013.01); *B65D 77/40* (2013.01); *B65D 83/0055* (2013.01); *B65D 2251/0015* (2013.01); *B65D 2251/0093* (2013.01)

(58) Field of Classification Search
 CPC ............ A61M 5/14593; A61M 11/008; A61M 2205/14264; A61M 2205/14252; A61M 2205/1426; A61M 2205/14204; B65D 25/42; B65D 51/22; B65D 51/226; B65D 73/0078; B65D 75/32; B65D 75/5877; B65D 75/70; B65D 83/0055; B65D 2251/0015; B65D 2251/0093; B05B 11/043; B05B 11/042; A61J 1/067; A61J 1/2093; A61J 1/1406; A61J 1/10; A61J 1/12; A61J 1/2096; A61J 1/1418; A61J 1/2024
 See application file for complete search history.

(56) References Cited

U.S. PATENT DOCUMENTS

| | | | | |
|---|---|---|---|---|
| 4,869,399 | A * | 9/1989 | Dubach | B65D 47/0814 222/83 |
| 4,884,703 | A * | 12/1989 | O'Meara | B65D 51/222 215/6 |
| 5,094,361 | A * | 3/1992 | Dubach | B65D 47/36 215/235 |
| 5,205,820 | A * | 4/1993 | Kriesel | A61M 5/1409 128/DIG. 12 |
| 5,228,592 | A * | 7/1993 | Pellerano | B65D 47/36 222/83 |
| 5,992,668 | A * | 11/1999 | Elliott | B65D 47/0804 215/228 |
| 6,460,781 | B1 * | 10/2002 | Garcia | A45D 37/00 222/107 |
| 7,780,636 | B2 * | 8/2010 | Radmer | A61M 5/14248 604/171 |
| 8,522,995 | B2 * | 9/2013 | Voss | B65D 47/065 220/277 |
| 2008/0073372 | A1 * | 3/2008 | Keller | A61J 1/2093 221/94 |
| 2009/0204096 | A1 * | 8/2009 | Kuroki | A61M 11/00 604/411 |
| 2011/0052459 | A1 | 3/2011 | Shibata et al. | |
| 2012/0241465 | A1 * | 9/2012 | Genosar | A61M 5/282 222/1 |
| 2014/0346071 | A1 * | 11/2014 | Genosar | A61J 1/00 206/438 |

FOREIGN PATENT DOCUMENTS

| | | |
|---|---|---|
| JP | 57-046763 | 3/1982 |
| JP | 8-198285 | 8/1996 |
| JP | 2001-328660 | 11/2001 |
| WO | WO 01/074291 | 10/2001 |
| WO | WO-2017091452 A1 * | 6/2017 ............ A61M 15/08 |

* cited by examiner

SEALING CONTAINER

This is a continuation of International Application No. PCT/JP2016/056318 filed Mar. 1, 2016 which claims the foreign filing priority based on Japanese Patent Application No. 2015-051527 filed Mar. 15, 2015, the entire contents of which are incorporated herein by reference.

TECHNICAL FIELD OF THE INVENTION

This invention relates to a sealing container for hermetically storing the contents therein.

BACKGROUND OF THE INVENTION

Conventionally, when a user performs an opening operation of a sealing container, the pressure of the liquid in a bag body of the container rises, and a sealing film of the bag body bulges toward a protrusion, and the sealing film is penetrated by the protrusion and thus the sealing film is opened, thereby the liquid inside the bag body flows out from the opening of the sealing film (see, for example, Patent Document 1).

CITATION LIST

Patent Document 1: International Publication No. WO 2008/010262 (U.S. Application Publication No. 2009/0204096)

SUMMARY OF INVENTION

Problem to be Solved by the Invention

However, in the case of the sealing container described in Patent Document 1 noted above, it is difficult for the user to grasp the degree of bulging of the sealing film when the user raises the pressure of the liquid inside the bag body by performing the opening operation, and thus it is difficult for the user to know the timing at which the sealing film is penetrated by the protruding unit. Therefore, it is difficult for the user to adjust the timing at which the liquid flows out since the liquid flows out at the same time when the sealing film is penetrated by the protruding unit.

Therefore, the present invention has been made to solve the problem noted above involved in the conventional technology, and it is an object of the present invention to provide a sealing container which can allow a user to freely adjust the timing at which the contents are discharged from the sealing container.

Means for Solving the Problem

The sealing container of the present invention is comprised of:
a housing unit for accommodating the contents therein,
a sealing film for sealing the housing unit,
an opening means so configured that at least a part of which is movable toward the sealing film and is capable of opening the sealing film,
an operation unit for performing an operation of moving the opening means, and
a discharge means configured to be capable of ejecting the contents from the housing unit at a timing different from a timing at which the opening means penetrates the sealing film by operating the operation unit.

Since the sealing container is configured in this way, it is possible for the user to perform only the operation of opening the sealing film by operating the operation unit, so that the user is able to arbitrarily adjust the timing at which the content is discharged.

Further, in the sealing container of the present invention, the contents can be discharged from the housing unit by performing an operation of discharging the content from the housing unit after the operation of the operation unit is performed.

Since the sealing container is configured in this way, the content is discharged at the timing when the user performs the operation of discharging the content from the housing unit, thus, the user can freely adjust the timing at which the content is discharged.

The sealing container of the present invention further includes a moving means for moving at least a part of the opening means penetrating through the sealing film in a direction to which separating from the sealing film.

With this configuration of the sealing container, when the contents are discharged from the housing unit, the opening means does not close the opening formed in the sealing film, so that it is possible to prevent the opening means from obstructing the discharge of the contents. For example, in the containers of the prior art, there is a problem in that when the liquid inside of the bag body flows out from the hole opened in the sealing film, the tip of the protrusion penetrating the sealing film is positioned in such a way to close the hole, thus the tip of the protruding part hinders the outflow of the liquid. The present invention can solve such a problem involved in the conventional technology.

Further, in the sealing container of the present invention, at least a part of the opening means is movable beyond the sealing film that is in a normal position.

Since the sealing container is configured in this way, the opening means can penetrate the sealing film that is in the normal position.

The sealing container of the present invention further includes an entry prevention means for preventing the opening means from further entering the sealing film by a predetermined entry length or more when the opening means penetrates the sealing film.

Since the sealing container is configured in this way, it is possible to prevent the opening means from entering the housing unit in an excessive degree when the opening means penetrates the sealing film.

The sealing container of the present invention further includes a space forming unit which is configured to form a space inside the housing unit to secure a penetration length into which the opening means enters the housing unit when the opening means penetrates the sealing film.

Since the sealing container is configured in this way, when the opening means penetrates the sealing film, it is possible to prevent the opening means from inadvertently contacting with the inner face side of the housing unit and scratching the housing unit.

Further, in the sealing container of the present invention, the opening means has a linear blade at least a part of which is bent, and a cut is formed in the sealing film by the blade.

With this arrangement, the blade of the opening means penetrates the sealing film in such a way that a linear cut in which at least a part thereof is bent is formed in the sealing film, and the sealing film is rolled up from the cut, thus the opening of the sealing film widely expands and the contents of the container can be discharged smoothly from the opening of the sealing film.

The sealing container of the present invention further includes a maintaining means for maintaining a state in which the opening of the sealing film is enlarged from the cut formed by the blade.

Since the sealing container is configured in this way, the state in which the opening of the sealing film is enlarged is maintained, and the contents of the container can be discharged smoothly from the opening of the sealing film.

The sealing container of the present invention further includes:

a front chamber into which the content discharged from the opening formed in the sealing film by the opening means enters, a discharge port for discharging the contents outward from the front chamber, and a confirmation means configured to be capable of confirming that the content has entered the front chamber.

Since the sealing container is configured in this way, because the contents discharged from the opening of the sealing film once enter the front chamber, it is possible to prevent the contents from being inadvertently discharged outwardly, and after the user operates the operation unit, the user can confirm via the confirmation means that the sealing film has opened, that is, the contents can be discharged. For example, in the container of the prior art, there is a problem in that when the user opens the sealing film by the protrusion, the user is not able to confirm that the liquid can flow out until the liquid inside the bag body actually flows out to the outside. The present invention can solve such a problem.

The sealing container of the present invention further includes:

a front chamber into which the content discharged from the opening formed in the sealing film by the opening means enters, a discharge port for discharging the contents from the front chamber toward the outside, and a check valve means for preventing the content, which is liquid, flowing from the front chamber toward the discharge port from flowing backward.

Since the sealing container is configured in this way, because the contents discharged from the opening of the sealing film once enter the front chamber, it is possible to prevent the contents from being accidentally discharged to the outside, and further it is possible to prevent reverse flow of the content that is flowing from the front chamber to the discharge port.

Further, in the sealing container of the present invention, the check valve means includes a film-shaped member configured to deform in accordance with the flow of the fluid.

Since the sealing container is configured in this way, the check valve means can be realized with use of simple elements such as a film-shaped member, and further, the check valve means can be established with a small size.

The sealing container of the present invention further includes:

a front chamber into which the content discharged from the opening formed in the sealing film by the opening means enters, and a discharge port for discharging the contents outward from the front chamber, where the front chamber is formed by the (first) sealing film and an operation film which is a second sealing film disposed to face the first sealing film where the operation film covers the opening means in a state where the opening means is operable.

Since the sealing container is configured in this way, the contents discharged from the opening of the sealing film once enter the front chamber, thus it is possible to prevent the contents from being accidentally discharged to the outside. Further, the front chamber can be configured by a simple structure of two sealing films, and the second sealing film can be used as the operation unit.

The sealing container of the present invention further includes a foldable plate-shaped member, where the operation of discharging the contents, which is liquid, from the housing unit is an operation conducted by sandwiching at least a part of the housing unit with the foldable plate-shaped member and raising the pressure of the contents in an inner area of the housing unit.

Since the sealing container is configured in this way, the user can easily perform the discharging operation of the contents, and the operation of raising the pressure of the contents can be realized by a simple element of the foldable plate-shaped member which is sandwiching the housing unit.

The sealing container of the present invention further includes:

a discharge pipe having a discharge port for discharging the contents outward, and a storage means configured to be capable of swinging with respect to the discharge pipe and capable of storing the discharge pipe, where at least a part of the discharge pipe is covered by the swinging movements of the storage means.

With this arrangement, when the user stores the discharge pipe by the storage means, since the movement of the user's finger operating the storage means is a swinging movement with respect to the discharge pipe, it is possible to prevent the tip of the discharge pipe from touching the fingers of the user. For example, in an application of a syringe (pre-filled syringe) which is a medical instrument, when a medical personnel stores an injection needle (discharge pipe) after using the syringe into a cap, a syringe needle may stick to his or her finger by mistake. However, when the present invention is applied to the syringe, such a problem can be solved.

Further, in the sealing container of the present invention, the storage means has a plate-like unit which sandwiches the discharge pipe from both sides.

Since the sealing container is configured in this way, the storage means swinging with respect to the discharge pipe can be realized with use of simple elements.

The sealing container of the present invention further includes a protection means for protecting the operation unit so that no external force is applied thereto before the operation unit is operated.

Since the sealing container is configured in this way, it is possible to prevent unnecessary application of an external force to the operation unit, thereby the opening is created in the sealing film.

The sealing container of the present invention further includes:

a discharge pipe having a discharge port for discharging the contents outward, and a storage means having a plate-shaped unit sandwiching the discharge pipe from both sides thereof and capable of housing the discharge pipe, where the protection means is the plate-shaped unit of the storage means which is capable of covering the operation unit together with the discharge pipe.

Since the sealing container is configured in this way, it is possible to cover the operation unit as well as to store the discharge pipe therein.

A disposable type sealing container of the present invention includes:

a cup-shaped housing unit for accommodating the contents therein, a sealing film that hermetically closes the opening of the housing unit, and an opening means configured to be capable of moving toward the sealing film and opening at least a part of the sealing film.

In this configuration of the sealing container, since the sealing film can be opened by using the opening means, it is possible for the user to easily open the container. For example, in the conventional technology, in a single-serving container filled with milk for coffee, gum syrup or the like, a film-like lid which blocks the opening of the container is opened by a user with tips of his/her fingers of both hands, which arises a problem in that it is difficult to open the single-serving container. However, in the present invention, since the sealing film can be opened by using the opening means, it is possible to easily open this type of container.

It is to be noted that the disposable type sealing container of the present invention further includes an air hole forming means configured to be capable of forming an air hole in the sealing film for allowing the air to flow into the housing unit other than the opening formed in the sealing film by the opening means.

In this configuration of the sealing container, when the contents in the housing unit are discharged from the opening formed in the sealing film, the air is introduced into the housing unit through the air hole, it is possible to discharge the contents smoothly from the opening formed in the sealing film.

It is to be noted that, in the disposable type sealing container of the present invention, the air hole forming means is provided in such a way to be movable toward the sealing film together with the movement of the opening means.

Since the sealing container is configured in this way, because the air hole can be formed simultaneously with opening the sealing film by using the opening means, the user can easily form the air hole in the sealing film.

It is to be noted that the disposable type sealing container of the present invention further includes a protection means for protecting the opening means from being subjected to an external force before the sealing film is opened by the opening means where the protection means is a lid member which is capable of covering the sealing film and the opening means and is also capable of being separable from the housing unit.

Since the sealing container is configured in this way, it is possible to prevent the sealing film from being scratched by inadvertently applying an external force to the sealing film or the opening means.

It is to be noted that, in the sealing container of the present invention, the opening means is provided in a manner to be incapable of separating from the housing unit or the sealing film.

With this arrangement of the sealing container, since the opening means is a member integral with the housing unit or the sealing film, loss of the opening means can be prevented, and also, when the user discards the sealing container after use, the opening means can be discarded as a member integral with the housing unit or the sealing film.

It is to be noted that the check valve means in the sealing container of the present invention includes:

a first space and a second space separated from one another by a partition are provided, and a fluid flowing from the first space toward the second space via a hole opened in the partition is prevented from flowing backward, and a film-shaped member covering the hole from the second space side is provided, where one end of the film-shaped member is fixed in the vicinity of the periphery of the hole and the other end of the film-shaped member conducts a deforming movement in response to the flow of the fluid.

Since the sealing container is configured in this way, the check valve means can be realized with use of simple elements such as a film-shaped member, and further, the check valve means can be achieved with a small size.

DESCRIPTION OF THE PREFERRED EMBODIMENTS

Figure 1:
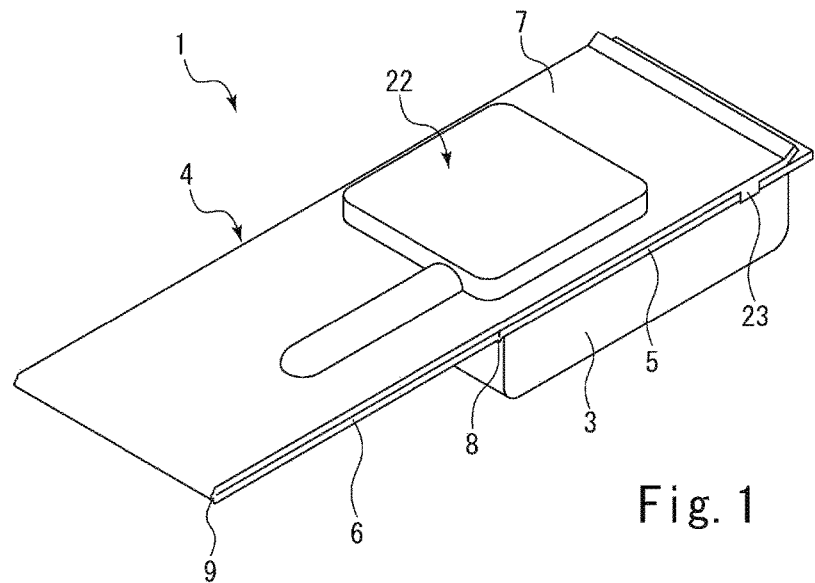
FIG. 1 is a perspective view showing a pre-filled syringe as an example of a sealing container of the first embodiment of the present invention.

Embodiments for carrying out the sealing container according to the present invention will be described below based on various examples. It should be noted that the configurations of the sealing container are not limited to that of the embodiments described in the following, and any changes or additions that are within the scope and not departing from the gist of the present invention will be included in the present invention.

[First Embodiment]

A sealing container according to the first embodiment of the present invention will be described with reference to FIGS. 1 to 16. In the drawings, reference number 1 is a pre-filled syringe as the sealing container of the first embodiment. The pre-filled syringe 1 is a disposable syringe which is provided in the market in a state in which medicinal solution (contents) is pre-filled, and it is a type of syringe which can be safely transported in a state where an injection needle 2 (discharge pipe) is attached thereto in advance.

Figure 2:
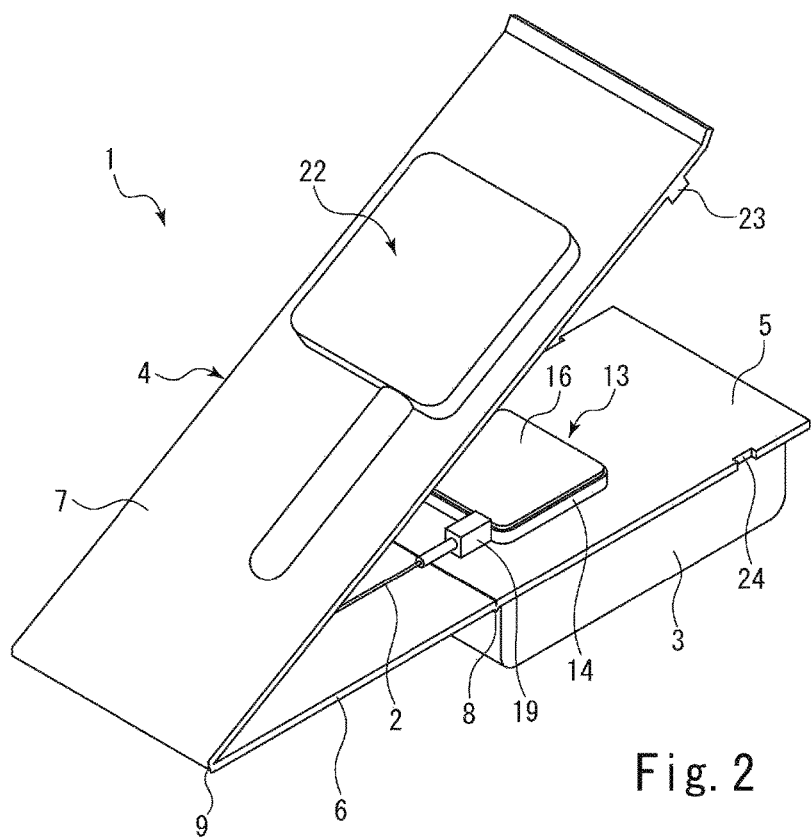
FIG. 2 is a perspective view showing a state in which a cover plate portion of the pre-filled syringe is opened.

As shown in FIGS. 1 and 2, the pre-filled syringe 1 includes an injection needle 2 for injecting a medical solution into a subject (in the first embodiment, a patient or the like), a bag-shaped member 3 (housing or accommodating unit: a member forming the accommodating space) filled with a medicine in the form of liquid corresponding to an amount of almost one use, and a plate-shaped member 4 (plate member) having a rectangular plate shape. It is to be noted that the injection needle 2 is made of a material such as metal. The injection needle 2 is housed in a state of being covered with the plate-shaped member 4 which is folded. Further, the bag-shaped member 3 is preferably made of a material such as a synthetic resin having flexibility and being easily deformable and further having plasticity.

Figure 3:
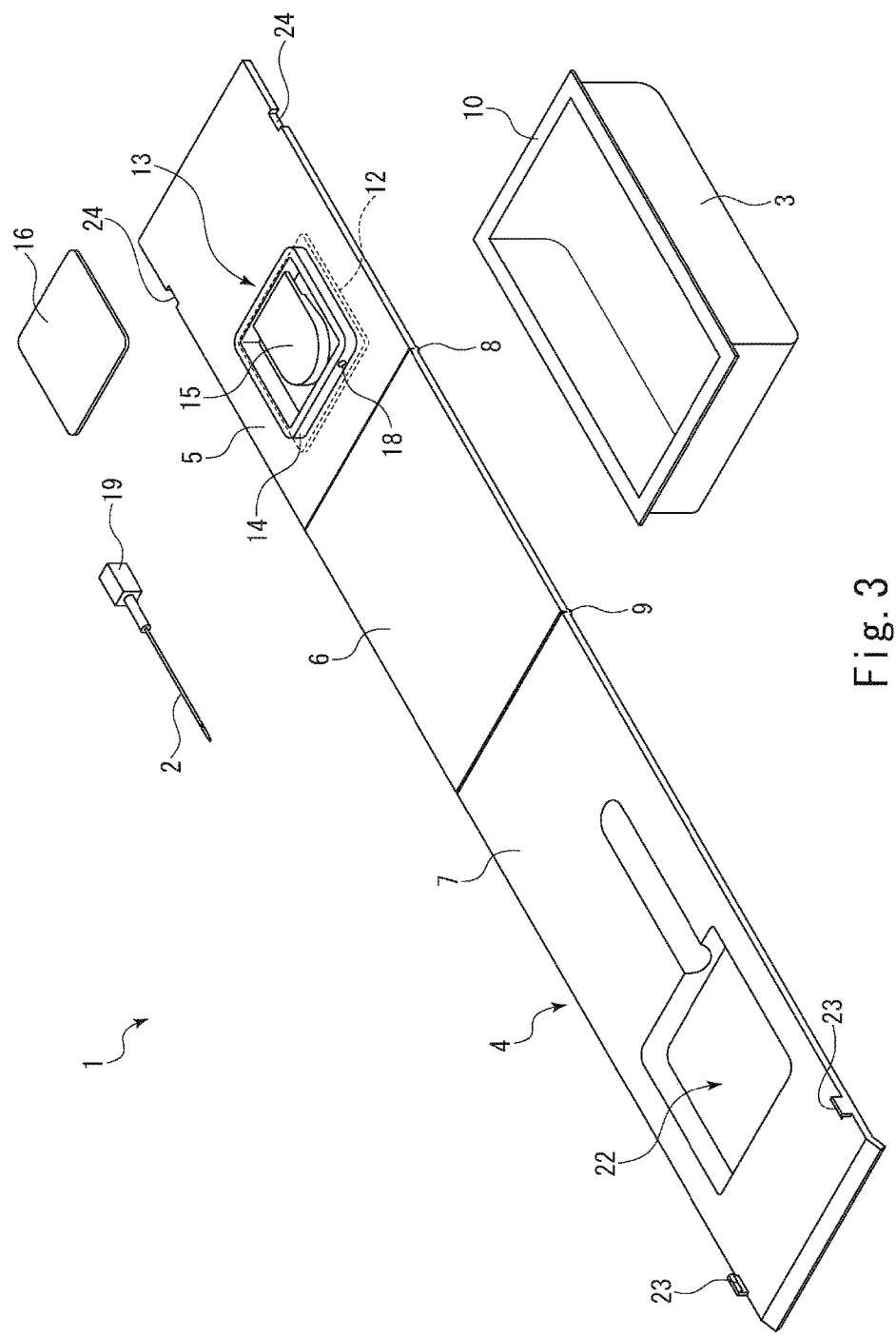
FIG. 3 is an exploded perspective view showing the pre-filled syringe.

As shown in FIG. 3, the plate-shaped member 4 is a single member having a rectangular shape, and two parts in the longitudinal direction thereof are so formed to be bendable. It is preferable that the plate-shaped member 4 is made of a material such as a synthetic resin that has flexibility but is hardly deformed. It should be noted that, in this disclosure, hereafter, an upper surface (the surface on the side visible in FIG. 3) of the plate-shaped member 4 is referred to as a first surface, and a lower surface (the surface on the side not visible in FIG. 3) of the plate-shaped member 4 is referred to as a second surface in the following descriptions.

The plate-shaped member 4 is configured by three plate members, i.e., a first plate portion 5 on which the bag-shaped member 3 is attached to the second surface (lower surface), a second plate portion 6 adjacent to the first plate portion 5, and a cover plate portion 7 adjacent to this second plate portion 6. It is to be noted that the first plate portion 5 and the second plate portion 6 can be bent with one another by a first bent portion 8, and the second plate portion 6 and the cover plate portion 7 can be bent with one another by a second bent portion 9.

In addition, the first plate portion 5 and the second plate portion 6 are formed to have substantially the same size (surface area). That is, the length dimension and the width dimension of the first plate portion 5 are substantially the same as the length dimension and the width dimension of the second plate portion 6. Further, when the plate-shaped member 4 is bent around the first bent portion 8, the second surface of the second plate portion 6 can be brought close to the second surface of the first plate portion 5 (see FIG. 10).

In addition, the cover plate portion 7 is formed to have a size (surface area) that is able to cover the first surface (upper surface) from the second plate portion 6 to the first plate portion 5. That is, the combined length dimension of the first plate portion 5 and the second plate portion 6 is substantially the same as the length dimension of the cover plate portion 7. It is to be noted that the width dimension of the cover plate portion 7 is substantially the same as the width dimensions of the first plate portion 5 and the second plate portion 6. In addition, when the plate-shaped member 4 is bent around the second bent portion 9, the first surface of the cover plate portion 7 can be brought close to the first surfaces of the first plate portion 5 and the second plate portion 6 (see FIGS. 1 and 8).

Further, the bag-shaped member 3 has a rectangular parallelepiped shape with its upper side opened. Since a peripheral edge rim 10 of the opening of the bag-shaped member 3 is bonded to the peripheral part (the halftone dot part shown in FIG. 5) of the second surface (lower surface) of the first plate portion 5, the bag-shaped member 3 is attached to the second surface of the first plate portion 5. Note that the bonding described in this disclosure may be a bonding using an adhesive, a bonding in which members are strongly pressed with one another to be crimped, or can be a bonding using other means as well.

Figure 5:
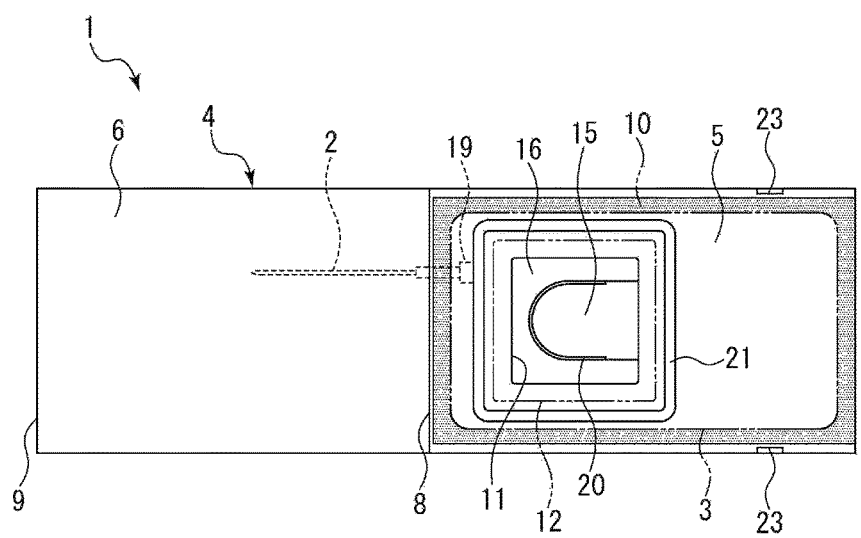
FIG. 5 is a bottom view showing the pre-filled syringe.

As shown in FIG. 5, in the center of the first plate portion 5 of the plate-shaped member 4, an opening unit 11 which is opened in a square shape (regular square) is formed. The opening unit 11 is closed by a sealing film (membrane) 12 attached to the second surface side of the first plate portion 5 (see FIG. 7). It is to be noted that the chemical liquid filled in the bag-shaped member 3 is maintained in a state in which it is sealed by the sealing film 12.

Figure 6:
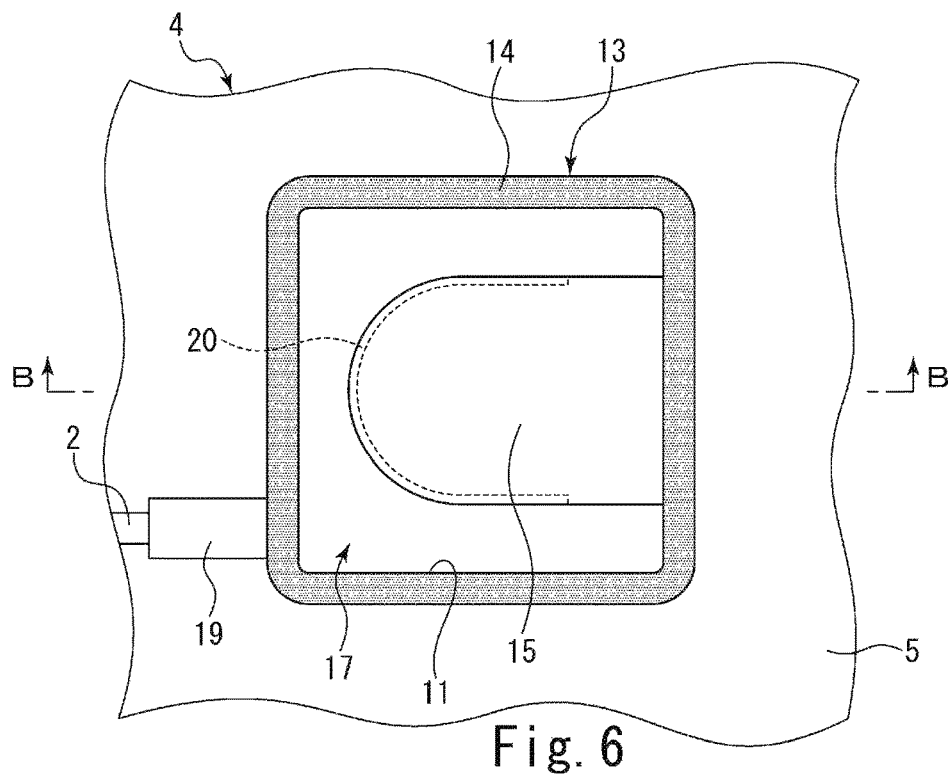
FIG. 6 is a plan view showing an opening operation unit of the pre-filled syringe.
Figure 7:
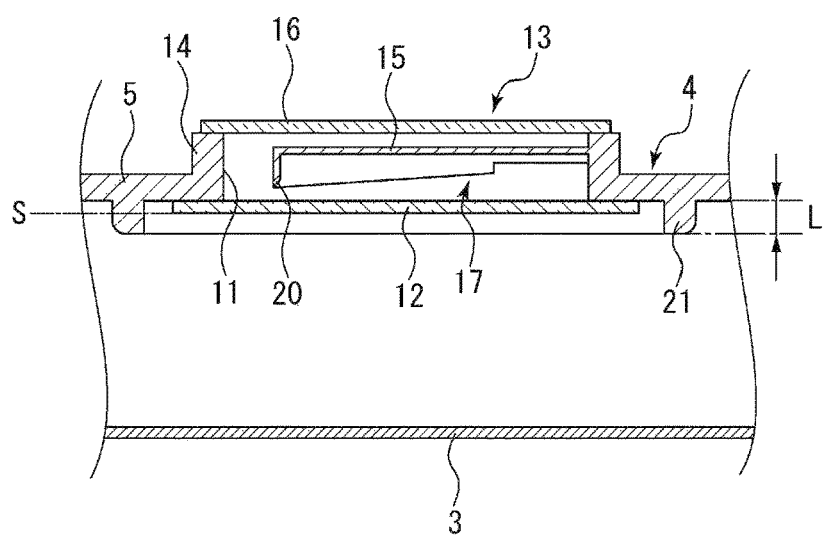
FIG. 7 is a cross-sectional view taken along the line B-B of FIG. 6 showing the opening operation unit of the pre-filled syringe.

As shown in FIGS. 6 and 7, on the first surface (upper surface) side of the first plate portion 5, an opening operation unit 13 is provided for a user (medical personnel etc. in the first embodiment) at a position corresponding to the opening unit 11 for performing an operation of opening the sealing film 12. The opening operation unit 13 has a frame 14 that protrudes upward in a quadrangular (square) shape in a plan view, in which an opening means 15 is formed in a manner to extend from a part of the inner peripheral surface of the frame 14 toward an inner area of the frame 14.

The opening means 15 is a protruding piece having a thin plate shape in which the edge on the tip side thereof is rounded in a semicircular shape. Further, the opening means 15 extends from one side of the frame 14 and is separated from the other three sides of the frame 14. Further, the opening means 15 is configured to be capable of swinging in the vertical direction (movable in the direction going close to the sealing film 12) with the base end side as a fulcrum. That is, although the opening means 15 is integrally formed with the plate-shaped member 4, it is elastically deformable because the opening means 15 is formed in a thin plate shape.

Further, on the upper end face of the frame 14 of the opening operation unit 13, an operation film 16 (operation unit) which can be pushed in when the user has to operate the opening means 15 is attached. It is to be noted that the peripheral edge of the operation film 16 is bonded to the upper end face (halftone dot part shown in FIG. 6) of the frame 14. Further, a space surrounded by the sealing film 12, the frame 14, and the operation film 16 configures a front chamber 17. In this way, the front chamber 17 can be formed by simple components with use of the two sealing films.

It is to be noted that the sealing film 12 and the operation film 16 are disposed so as to be parallel to each other when viewed from the side. Further, the opening means 15 is disposed in the front chamber 17 which is arranged between the sealing film 12 and the operation film 16. Further, the opening means 15 is provided at a position away from the sealing film 12. Further, the opening means 15 is arranged so as to be parallel to the sealing film 12 and the operation film 16 in a side view.

In addition, an injection needle 2 is attached to the opening operation unit 13. A communication hole 18 for allowing the chemical liquid to pass from the front chamber 17 toward the injection needle 2 is provided in the frame 14 of the opening operation unit 13 (see FIG. 3). Further, the injection needle 2 is connected to a part of the opening operation unit 13 corresponding to the communication hole 18 via a check valve 19. It is to be noted that when the chemical liquid flows into the front chamber 17 from the bag-shaped member 3, the chemical liquid is discharged from the opening (discharge port) at the tip of the injection needle 2.

It is preferable that the sealing film 12 is formed of a material such as a synthetic resin which is difficult to deform. The sealing film 12 closes the opening unit 11 in a state in which the tension is applied thereto. Further, it is preferable that the operation film 16 is formed of a material such as a synthetic resin which is easily elastically deformed. At least the operation film 16 is made of a material which is more easily elastically deformed than the material forming the sealing film 12. Further, the operation film 16 is a transparent member. When the operation film 16 is pushed by the user's finger, it is possible to push down the opening means 15 together with the operation film 16 (see FIG. 9). The sealing film 12 can be opened by this push-down movement of the opening means 15.

As shown in FIG. 7, the opening means 15 is provided with a blade 20 which is downwardly protruding therefrom. The lower end edge of the blade 20 has an acute shape so that it can penetrate the sealing film 12. The blade 20 extends from the edge of the leading end of the opening means 15 to the edges of the side ends. The lower end side of the blade 20 is inclined so as to go down from the base end side of the opening means 15 toward the distal end side of the opening means 15. That is, when the opening means 15 is pushed down, the blade 20 on the distal end side of the opening means 15 is first brought into contact with the sealing film 12, and when the opening means 15 is further pushed down, a cut is formed on the sealing film 12 (see FIG. 9).

As shown in FIG. 6, the blade 20 is formed in a U-shape (horseshoe shape) in a plan view. As the blade 20 penetrates (severs) the sealing film 12, a U-shaped (horseshoe shaped) cut (opening), that is, a line like cut which is at least partially curved is formed. It is to be noted that the sealing film 12 is rolled from this cut, so that the opening created on the sealing film 12 widens largely, so that the chemical solution can be smoothly discharged from the opening of the sealing film 12.

As shown in FIG. 7, the blade 20 of the opening means 15 can enter the bag-shaped member 3 from the outside of the bag-shaped member 3 beyond the sealing film 12 which is at the steady (normal) position S. It is to be noted that on the second surface of the first plate portion 5 of the plate-shaped member 4, a ridge 21 (space forming unit) protruding from the second surface are provided in a manner to surround the opening unit 11 and the sealing film 12. In addition, each ridge 21 has a projecting length L. By providing the ridge 21 in this manner, when the bag-shaped member 3 is deformed, it is possible to prevent the inner surface (bottom surface or the like) of a part of the bag-shaped member 3 from being approached (contacted) by the sealing film 12. Therefore, even if the blade 20 of the opening means 15 passes through the sealing film 12, the bag-shaped member 3 is prevented from being touched by the blade 20. In other words, since the ridge 21 has the projecting length L, a sufficient space is created for securing the penetration length for the blade 20 of the opening means 15 to enter the inside of the bag-shaped member 3 beyond the sealing film 12. Since this space is secured, when the blade 20 of the opening means 15 penetrates the sealing film 12, it is possible to prevent the opening means 15 erroneously comes into contact with the inner surface side of the bag-shaped member 3, thereby enabling to avoid the bag-shaped member 3 from being damaged.

In addition, the opening means 15 is a unit integrally formed with the plate-shaped member 4 (the frame 14) and is a unit having flexibility. Since the opening means 15 is formed to be thinner than the plate-shaped member 4, it is easy to bend around the base end side of the opening means 15. However, the rigidity of the opening means 15 is designed such a degree of rigidity that it does not bend beyond the projecting length L of the ridge 21. By thus defining the rigidity of the opening means 15, it is possible to prevent the opening means 15 from entering too much into the bag-shaped member 3 by a predetermined entry length or more. That is, an entry prevention means of the first embodiment is created in this manner. It is to be noted that the rigidity of the opening means 15 is determined based on the average pressing force produced when the user pushes the operation film 16 with use of the thumb.

Figure 4:
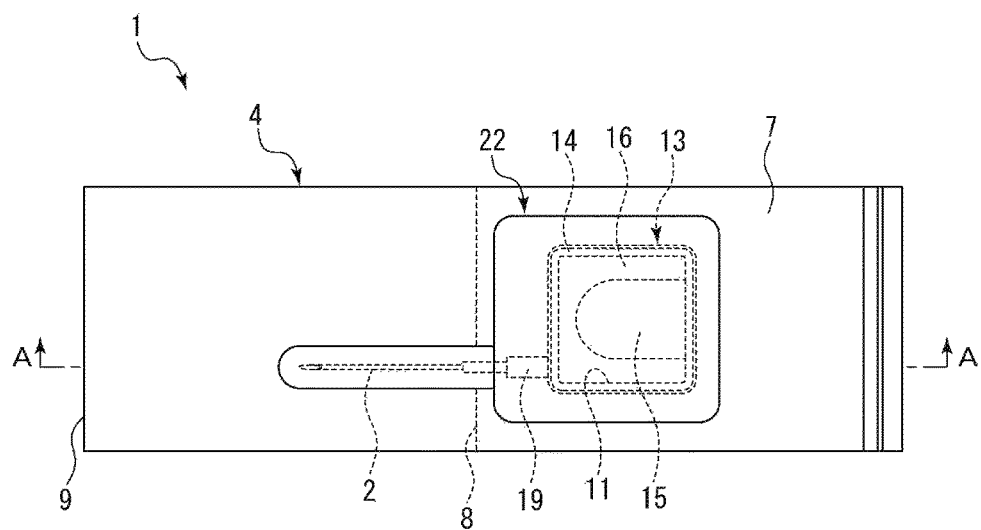
FIG. 4 is a plan view showing the pre-filled syringe.

As shown in FIG. 4, the injection needle 2 connected to the opening operation unit 13 extends from the first plate portion 5 to the second plate portion 6 side beyond the first bent portion 8. Further, in a plan view, the injection needle 2 is provided at a position displaced toward one side (lower side of the page of FIG. 4) from the center position in the width direction of the plate-shaped member 4.

As shown in FIG. 3, on the cover plate portion 7, there is provided with a storage 22 which is configured to be capable of storing the opening operation unit 13 and the injection needle 2. The storage 22 is a recessed unit formed by depressing a part of the cover plate portion 7 from the first surface side. It is to be noted that the storage 22 has a rectangular recessed unit (protection means) for housing the opening operation unit 13 and a linear recessed unit (storage means) for storing the injection needle 2 therein.

Figure 8:
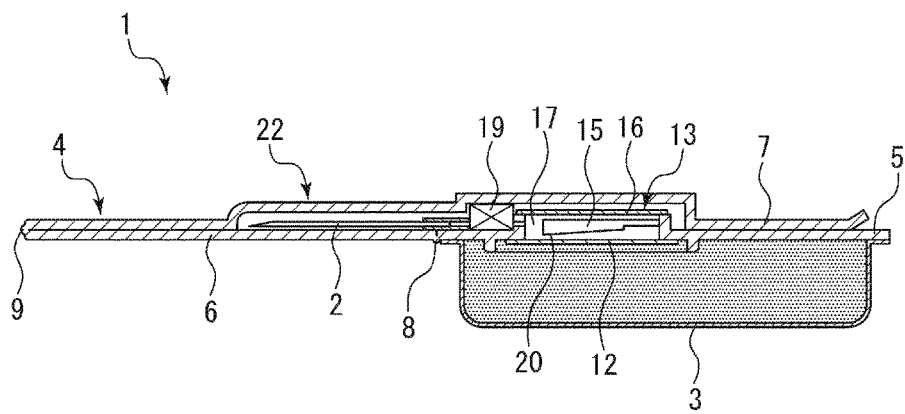
FIG. 8 is a cross-sectional view taken along the line A-A in FIG. 4 showing the pre-filled syringe.

As shown in FIG. 8, when the pre-filled syringe 1 is in a transporting state (a state in which it can be safely transported), the first bent portion 8 is in a non-bent state where it is not bent, and the second bent portion 9 is in a bent state where it is bent. In this transporting state, the first plate portion 5 and the second plate portion 6 are in a flat state, and the second plate portion 6 is arranged at a position close to the injection needle 2. It is to be noted that, in this state, the bending angle of the second bent portion 9 is approximately 180 degrees. Further, the first surface of the cover plate portion 7 is in contact with the first surfaces of both the first plate portion 5 and the second plate portion 6.

In this transporting state, the opening operation unit 13 and the injection needle 2 are in a state in which they are covered with the cover plate portion 7 and stored in the storage 22. The distal end side of the injection needle 2 is covered in such a way as to be sandwiched between the cover plate portion 7 and the second plate portion 6. Since the opening operation unit 13 is covered by the cover plate portion 7 in this manner, it is possible to avoid a situation where an external force is unintentionally applied to the operation film 16, and the opening means 15 is pressed, and as a result, the sealing film 12 is opened. In addition, since the injection needle 2 is covered by the cover plate portion 7 and the second plate portion 6, the pre-filled syringe 1 can be safely transported.

As shown in FIG. 3, hooking claws 23 are provided on both side parts in the vicinity of the end part of the cover plate portion 7. Further, claw fixing units 24 which are capable of engaging with the hooking claws 23 are provided on both side parts near the end part of the first plate portion 5. It is to be noted that the hooking claw 23 is a projecting piece which is projected from the side part of the cover plate portion 7 toward the first face side, and the claw fixing unit 24 is a cut-out portion formed by cutting out the side end part of the first plate portion 5. The hooking claw 23 is latched with respect to the claw fixing unit 24 in a detachable manner.

As shown in FIG. 1, when the pre-filled syringe 1 is in the transporting state, the hooking claw 23 of the cover plate portion 7 is hooked on the claw fixing unit 24 of the first plate portion 5, so that the cover plate portion 7 is prevented from accidentally separating from the first plate portion 5. Furthermore, since the cover plate portion 7 is disposed so as to straddle the first bent portion 8 extending from the second plate portion 6 to the first plate portion 5, it is possible to prevent the first bent portion 8 from being inadvertently bent.

Further, since the end edge of the cover plate portion 7 is bent (curved) in a direction that separates from the first plate portion 5, this edge is capable of allowing a user to put his or her fingers thereon. Thus, when the user is going to use the pre-filled syringe 1, by hooking the finger on the edge of the cover plate portion 7, the hooking claw 23 can be unhooked from the claw fixing unit 24. Then, the user can separate (open) the cover plate portion 7 from the first plate portion 5 and the second plate portion 6 (see FIG. 2).

Figure 9:
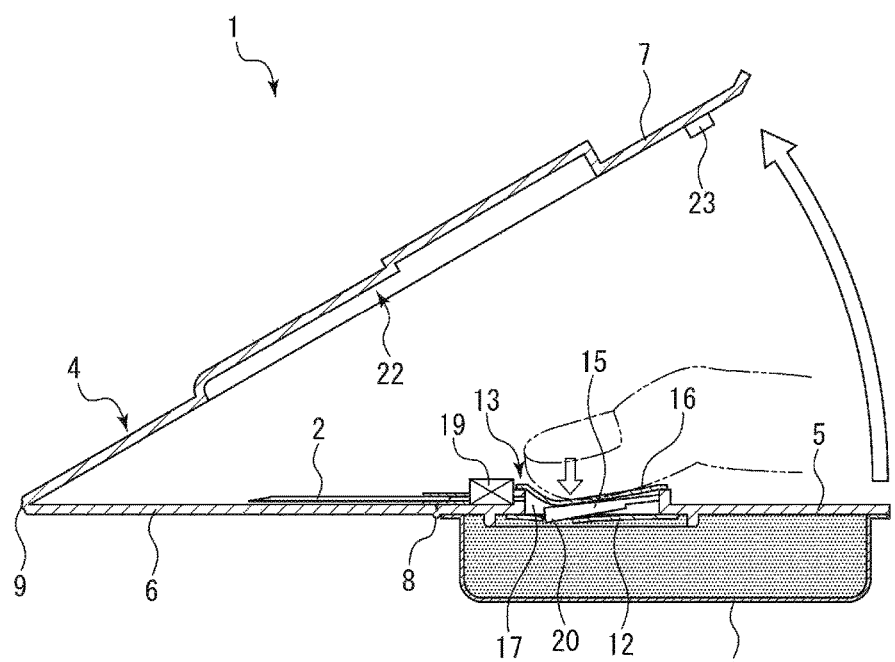
FIG. 9 is a side cross-sectional view showing the pre-filled syringe during an opening operation conducted by a user.

As shown in FIG. 9, when the cover plate portion 7 is opened, the opening operation unit 13 is exposed. In this state, when the user presses the operation film 16 with the thumb, the opening means 15 is pushed down, the blade 20 passes through the sealing film 12, and the sealing film 12 is opened. Then, when the sealing film 12 is opened, the chemical solution in the bag-shaped member 3 can flow out to the front chamber 17. It is to be noted that since the opening operation can be performed while the user touches the opening means 15 through the operation film 16, the user can grasp the timing at which the sealing film 12 is opened.

Figure 10:
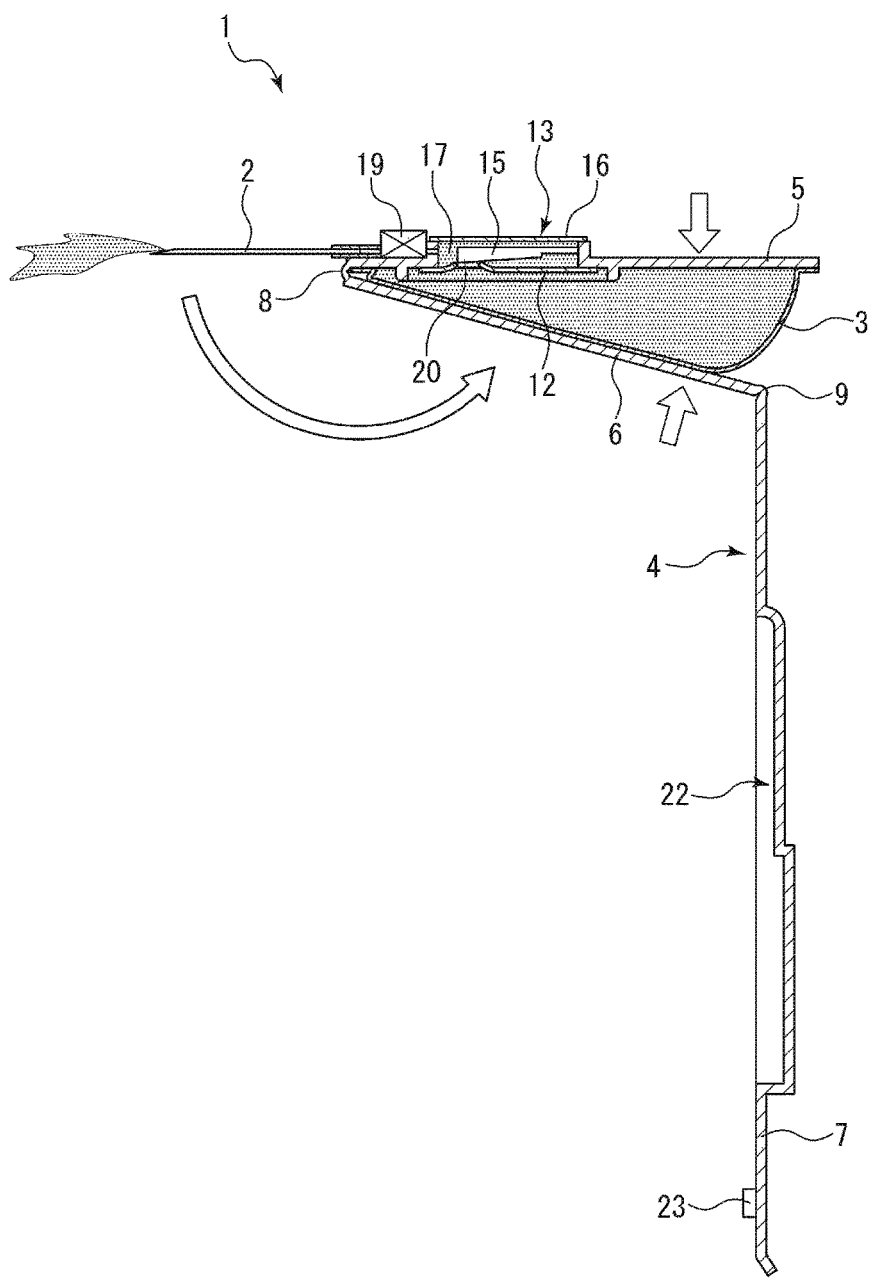
FIG. 10 is a side cross-sectional view showing a use state of the pre-filled syringe.
Figure 11:
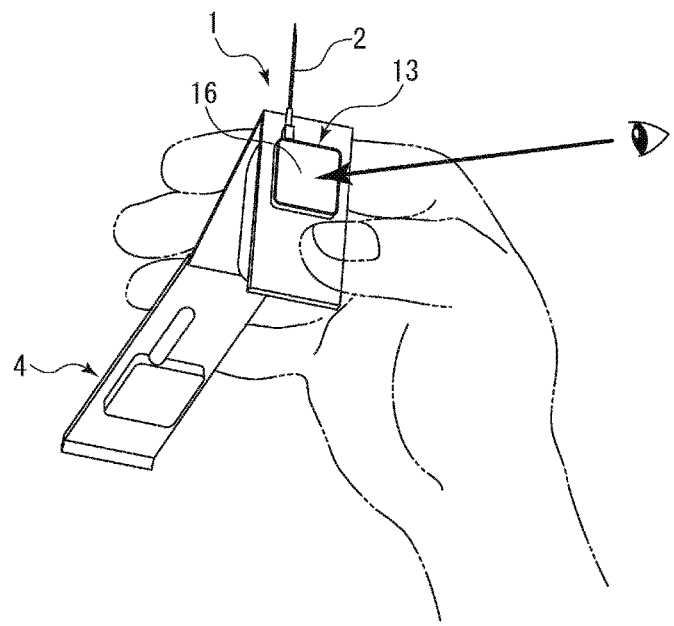
FIG. 11 is a view showing an example of use state in which the user confirms the opened state of the sealing film of the pre-filled syringe.
Figure 12:
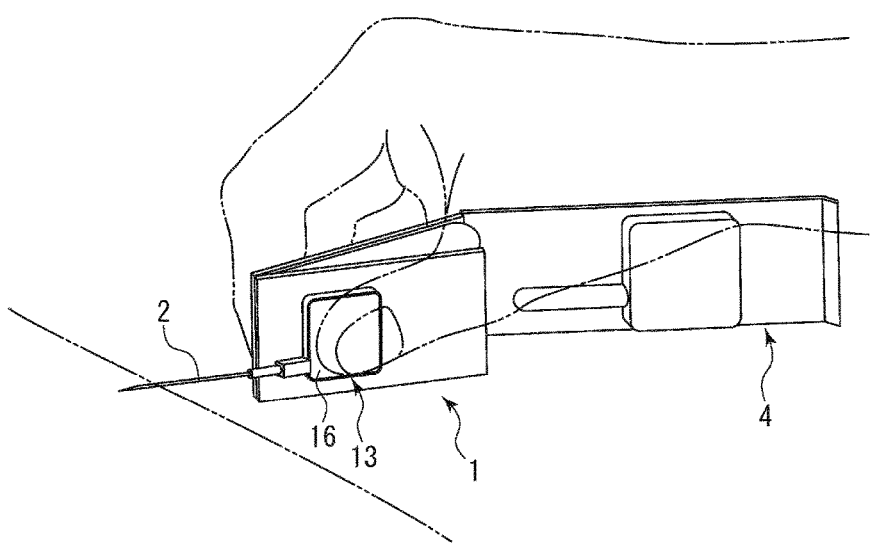
FIG. 12 is a diagram showing an example of use of the pre-filled syringe.

Further, when the user releases his/her thumb from the operation film 16, the opening means 15 returns to the normal position (retracted position) separated from the sealing film 12 by its elastic force (see FIG. 10). As a result, the opening means 15 is separated from the opening formed in the sealing film 12, so that the opening means 15 will not interfere the chemical solution in the bag-shaped member 3 from being discharged to the front chamber 17. It is to be noted that the fact that the opening means 15 has an elastic force constitutes the moving means of the first embodiment.

As shown in FIG. 10, the user further swings (rotates) the cover plate portion 7, whereby the second plate portion 6 is separated from the injection needle 2. Then, the second plate portion 6 is pivoted about the first bent portion 8, and as a result, the second surface of the second plate portion 6 comes close to the second surface of the first plate portion 5. When the second plate portion 6 approaches the first plate portion 5 as described above, the bag-shaped member 3 is sandwiched between the first plate portion 5 and the second plate portion 6. When the user pinches the bag-shaped member 3 that is in the state of being sandwiched between the first plate portion 5 and the second plate portion 6, the pressure of the chemical liquid in the bag-shaped member 3 is increased, and the chemical liquid is discharged through the opening of the sealing film 12 to the front chamber 17.

It is to be noted that since the operation film 16 (confirmation means) is a transparent member, the user can confirm whether or not the chemical solution has flowed into the front chamber 17 via the operation film 16. That is, it is possible for the user to confirm via the operation film 16 that the sealing film 12 is opened and injection of the medical solution becomes possible (see FIG. 11). In addition, since the user can perform the opening operation while visually recognizing the movement of the opening means 15 through the operation film 16, the user can grasp the timing at which the sealing film 12 is opened.

Further, when the user strongly pinches the bag-shaped member 3 by pressing the first plate portion 5 and the second plate portion 6, the chemical solution flows out from the opening of the tip of the injection needle 2 that is communicated with the front chamber 17. In the case of injecting the medical solution to the subject, firstly, the sealing film 12 is opened, and it is confirmed that the inside of the front chamber 17 is filled with the medical solution via the operation film 16. At this confirming stage, all the air in the front chamber 17 is discharged from the opening at the tip of the injection needle 2. Thereafter, when inserting the injection needle 2 in the subject and strongly pinching the bag member 3 with the first plate portion 5 and the second plate portion 6, it is possible to inject the medical solution into the subject (see FIG. 12). It is to be noted that since the injection needle 2 is provided at a position displaced to one lateral side from the center position in the width direction of the plate-shaped member 4, it is easy to insert the injection needle 2 into the target person because the plate-shaped member 4 hardly hits the target person.

Figure 13:
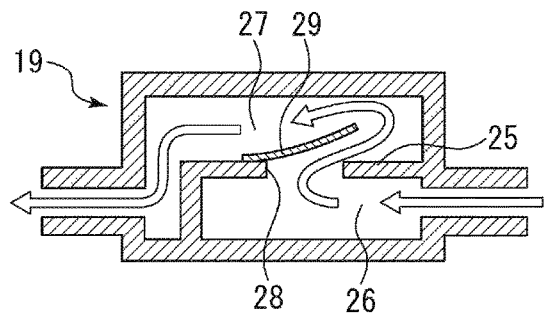
FIG. 13 is a side cross-sectional view showing a check valve in an open state.
Figure 14:
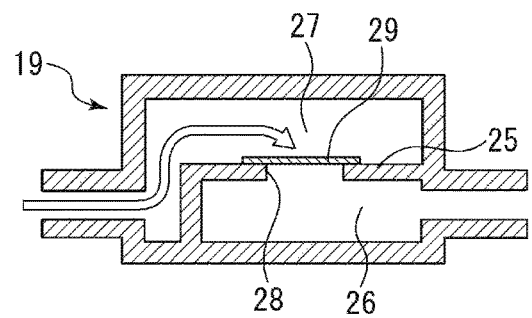
FIG. 14 is a side cross-sectional view showing the check valve in a closed state.

In the first embodiment, the injection needle 2 communicates with the front chamber 17 via the check valve 19 (check valve means). The check valve 19 is configured to prevent the chemical liquid, that is flowing from the front chamber 17 toward the opening at the tip of the injection needle 2, from flowing backward. As shown in FIG. 13, the check valve 19 is provided with a partition wall 25 (partition) which partitions the internal space of the check valve. Inside the check valve 19, a first chamber 26 (first space) and a second chamber 27 (second space) partitioned by the partition wall 25 are provided. It is to be noted that the first chamber 26 is communicated with the front chamber 17 and the second chamber 27 is communicated with the injection needle 2.

Figure 15:
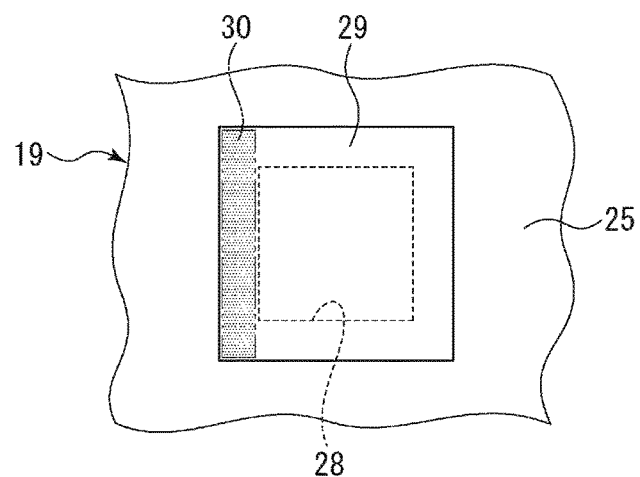
FIG. 15 is a plan view showing a film member of the check valve.
Figure 16:
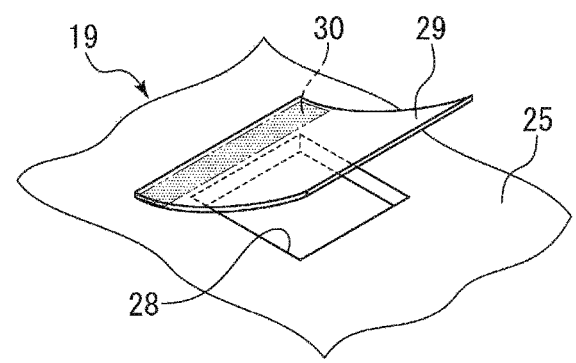
FIG. 16 is a perspective view showing the film member of the check valve.

As shown in FIG. 15 and FIG. 16, a minute hole 28 is penetrated through the partition wall 25. It is configured that the chemical solution can pass from the first chamber 26 to the second chamber 27 through the hole 28. On the side of the second chamber 27 of the hole 28, a film member 29 for covering the hole 28 is provided. It is to be noted that the hole 28 has a rectangular shape, and the film member 29 also has a rectangular shape (regular square) corresponding to the shape of the hole 28. Further, the film member 29 has an area larger than the area of the hole 28, so that the entire hole 28 can be closed by the film member 29. The one entire side of this film member 29 is an adhesive unit 30 (fixed unit) bonded (fixed) to the partition wall 25 in the vicinity of one side of the hole 28. The film member 29 is configured to be turned (deformed) around the fixed adhesive unit 30 in a direction that separates from the hole 28. It is to be noted that the film member 29 is made of a material such as a synthetic resin which is easily elastically deformed.

Furthermore, when the user strongly pinches the bag-shaped member 3 with use of the first plate portion 5 and the second plate portion 6, the pressure of the chemical liquid flowing into the first chamber 26 from the front chamber 17 is increased and the film member 29 is rolled up, and as a result, the chemical solution flows into the second chamber 27 through the hole 28 (see FIG. 13). Then, the chemical solution is caused to flow out from the opening of the tip of the injection needle 2 via the second chamber 27.

Further, when the user weakens the force of pinching the bag-shaped member 3 with use of the first plate portion 5 and the second plate portion 6, the pressure of the bag-shaped member 3 is decreased and the shape of the bag-shaped member 3 is restored, which may cause the air flows toward inside from the opening at the tip of the injection needle 2. At this time, the pressure of the chemical solution in the first chamber 26 is decreased, and as a result, the film member 29 goes down and closes the hole 28 in accordance with the flow of the chemical liquid flowing from the second chamber 27 to the first chamber 26 (see FIG. 14). In this way, by closing the hole 28 with the film member 29, it is possible to prevent the external air from entering the front chamber 17 and the bag-shaped member 3. Furthermore, with use of the film member 29 covering the hole 28, it is possible to realize the check valve 19 with use of simple components, and it is possible to achieve the check valve 19 with a small size.

As shown in FIG. 10, by strongly pinching the bag-shaped member 3 with use of the first plate portion 5 and the second plate portion 6, it is possible to inject almost all of the chemical solution in the bag-shaped member 3 to the subject. In the pre-filled syringe 1 of the first embodiment, since the medicinal solution can be injected by a finger gripping operation, such an operation can be performed more easily than a conventional syringe configured by a syringe barrel and a plunger syringe.

Also, after the operation of injecting the medical solution to the subject is completed, the pre-filled syringe 1 is separated from the subject, and the injection needle 2 is stored in the storage 22 again. When storing the injection needle 2, the second plate portion 6 is swung (rotated) in a direction to separate the second surface of the second plate portion 6 from the second surface of the first plate portion 5. Then, the second plate portion 6 is swung around the first bent portion 8 so as to return to the flat state in which the first plate portion 5 and the second plate portion 6 are flush with one another. Further, the cover plate portion 7 is swung around the second bent portion 9, and the first surface of the cover plate portion 7 is brought close to the first surface of the first plate portion 5 and the second plate portion 6. As a result, the injection needle 2 and the opening operation unit 13 are stored in the storage 22 of the cover plate portion 7, and further, the hooking claw 23 of the cover plate portion 7 is hooked on the claw fixing unit 24 of the first plate portion 5. In this manner, it is possible to return the pre-filled syringe 1 to the transporting state again. In addition, since the injection needle 2 is stored in the storage 22, the medical solution remaining in the bag-shaped member 3 will not drip from the injection needle 2.

According to the pre-filled syringe 1 of the first embodiment, when the user stores the injection needle 2 in the storage 22 of the cover plate portion 7, such a movement of the user's finger operating the cover plate portion 7 is a movement that rotates around the injection needle 2 so that it is possible to prevent the tip of the injection needle 2 from touching the user's fingers. For example, in the conventional syringe, when the injection needle is stored in the cap, since the movement of the user's fingers linearly moves with respect to the injection needle 2, there arises a problem in that the injection needle 2 may stick to his/her finger by mistake. However, the pre-filled syringe 1 of the first embodiment can solve such a problem.

Further, since the injection needle 2 is sandwiched and stored by the cover plate portion 7 and the second plate portion 6, the storage means swinging with respect to the injection needle 2 can be realized with use of simple elements. In addition, since the cover plate portion 7 and the second plate portion 6 can not be separated relative to the injection needle 2, it is possible to prevent the storage means from being lost. Further, the opening operation unit 13 can be covered with the cover plate portion 7 together with the storing operation of the injection needle 2. Further, by swinging the cover plate portion 7 around the second bending unit 9, the tip of the injection needle 2 is first stored in the storage 22, so that the injection needle 2 can be stored safely. It is to be noted that in the first embodiment, the whole of the injection needle 2 is stored in the storage 22, however, it is also possible that at least the tip of the injection needle 2 may be stored in the storage 22.

As has been described above, in the pre-filled syringe 1 of the first embodiment, the user conducts the pushing operation on the opening operation unit 13 so that the opening means 15 passes through the sealing film 12. Since the timing at which the sealing film 12 is passed through by the opening means 15 and the timing at which the medicinal solution can be discharged from the bag-shaped member 3 are different from one another, it is possible for the user to perform only the operation of opening the sealing film 12, so the user arbitrarily adjusts the timing at which the medical solution is discharged from the bag-shaped member 3. It is to be noted that in the first embodiment, a discharge means is constituted by the bag-shaped member 3 made of flexible material, and the first plate portion 5 and the second plate portion 6 sandwiching the bag-shaped member 3.

Further, since the user can eject the medicinal solution from the bag-shaped member 3 by performing the operation to eject the medicinal solution from the bag-shaped member 3 after the user performs the pressing operation of the opening operating unit 13, and thus, the medical solution is discharged at the timing at which performing the operation of discharging from the bag-shaped member 3, it is possible that the user freely adjusts the timing at which the medical solution is discharged.

Further, since the blade 20 of the opening means 15 penetrating the sealing film 12 is moved in the direction that is departing from the sealing film 12, when the chemical solution is discharged from the bag-shaped member 3, it is possible to prevent the opening means 15 from obstructing the discharge of the chemical solution since the opening formed in the sealing film 12 is not blocked by the opening means 15.

Further, at least the blade 20 of the opening means 15 can move beyond the sealing film 12 which is at the normal (steady) position S from the outside of the bag-shaped member 3, so that the blade 20 of the opening means 15 can penetrate the sealing film 12 provided at the stationary position S.

It is to be noted that in the first embodiment, the blade 20 is so configured to penetrate the sealing film 12 which is at the normal position S. However, other opening modes may also be used. For example, it is also possible that, before the user conducts the operation for opening the sealing film 12, the bag-shaped member 3 is strongly pinched with use of the first plate portion 5 and the second plate portion 6 to raise the pressure of the liquid inside the bag-shaped member 3, and thus at least a part of the sealing film 12 is moved from the normal position S to the position that is bulging toward the inside of the front chamber 17, thereby the bulged sealing film 12 is cut by the blade 20. In such an opening mode, by opening the sealing film 12 after sufficiently raising the pressure of the liquid inside the bag-shaped member 3, it is possible for the user to discharge (eject) the liquid to the outside at the same time as the timing at which the user opens the sealing film 12. In addition, it is also possible that, by lightly pinching the bag member 3 with use of the first plate portion 5 and the second plate portion 6, the pressure of the liquid inside the bag member 3 is raised so as to apply a tension to the sealing film 12, then the blade 20 penetrates the sealing film 12 to which the tension is applied.

It is to be noted that in the first embodiment, the blade 20 is formed in a U-shape (horseshoe shape) in a plan view. However, if the blade 20 has a linear shape in which at least a part thereof is bent (curved), the blade 20 may have other shapes as well. For example, the blade 20 may be formed in an S shape, a V shape, an X shape, a Y shape, or the like in a plan view.

In addition, in the first embodiment, since the chemical solution flowing out from the opening of the sealing film 12 once enters the front chamber 17, it is possible to prevent the chemical solution from accidentally flowing out to the outside. Further, it is possible for the user to confirm that the sealing film 12 has opened, that is, the user can confirm that the chemical solution can flow out from the injection needle 2 by watching it through the transparent operation film 16 after performing the pressing operation of the operation unit 13.

Further, in the first embodiment, the operation of discharging the medical solution (liquid) from the bag-shaped member 3 is an operation performed by the user by simply sandwiching the bag-shaped member 3 with use of the bent plate-shaped member 4 so that the pressure of the medical solution inside the bag-shaped member 3 is increased. Thus, the user can easily perform the discharging operation of the medical solution, and further, the operation of increasing the pressure of the medical solution can be performed by using a simple element of the bendable plate-shaped member 4 that sandwiches the bag-shaped member 3.

Further, in the first embodiment, since the opening means 15 is provided in a state in which it is relatively incapable of separating with respect to the bag-shaped member 3 or the sealing film 12, that is, the opening means 15 is integrally formed with the bag-shaped member 3 or the sealing film 12, it is possible to prevent the opening means 15 from being lost. Further, when the user discards the pre-filled syringe 1 after use, since the opening means 15 is integrally formed with the bag-shaped member 3 or the sealing film 12, it can be disposed all together as a single integral component. It should be noted that the relatively non-separable state described with respect to the first embodiment includes not only a mode in which the two members are directly connected with each other but also includes a mode in which the two members are integrally connected via the third member.

It is to be noted that since the pre-filled syringe 1 in the first embodiment has the plate-shaped member 4, it is possible to secure a sufficient area for indicating various kinds of information such as a chemical name, a concentration ratio, an expiration date, and the like. Further, since the pre-filled syringe 1 becomes unusable by a single use, there is no problem that the syringe after use is reused by a drug abuser or the like.

It is to be noted that since the medical solution inside the bag-shaped member 3 can be conveyed in a state of being completely sealed by the sealing film 12, airtightness can be maintained even when the external air pressure changes during the transportation, thus, leakage of medical solution and the like can be effectively prevented. Moreover, because of the airtightness, air bubbles and the like will not be mixed into the medical solution. Further, in the pre-filled syringe 1, the gas barrier property is enhanced as compared with the conventional pre-filled syringe which is sealed by using a screw cap or the like, so that it can withstand during long-term storage. For example, the storage life of the conventional pre-filled syringe is about one year, but when the pre-filled syringe 1 of the first embodiment is used, a longer term storage life can be realized.

It is to be noted that in the first embodiment noted above, although the operation film 16 is a transparent member, the operation film 16 may be a member having at least a light-transmitting property, and it is not necessary to be perfectly transparent. For example, the operation film 16 may be a transparent member with color, or a member that can scatter light by preventing linear transmission of light beams. Furthermore, the confirmation means need not be the transparent operation film 16, but can be a operation film using a member which changes its color when it contacts the liquid. When such a member constitutes the operation film, due to a change in the color of the operation film, it is possible to confirm that the liquid has flowed out to the front chamber 17. Further, it is also possible to provide a floating member (a member of conspicuous color) floating on the liquid in the front chamber 17, and the user visually recognizes the operation of the floating member via the operation film 16, so that the user can confirm whether or not the liquid has flowed out to the inside of the front chamber 17.

It is to be noted that in the first embodiment noted above, the operating film 16 (operating unit) and the blade 20 (opening means 15) are separate members, however, the operating film 16 and the blade 20 may be formed as an integral member. For example, the unit of the operation film 16 is made of a material such as elastomer which is easily elastically deformed, the unit of the blade 20 is made of a hard synthetic resin or the like, and the operation film 16 and the blade 20 are formed as an integral member via a two-colors molding (different material molding) process.

It is to be noted that, as shown in FIG. 6, the opening operation unit 13 (the frame 14) has a quadrangular shape (square shape) in a plan view, however, the shape of the opening operation unit 13 can be a circular shape or an elliptical shape, or any other shapes may be used as long as such a shape is a one for the user to easily press it with the thumb.

It is to be noted that, as shown in FIG. 15 and FIG. 16, the film member 29 covering the hole 28 of the check valve 19 has a rectangular shape, however, the film member 29 may have a circular shape, a triangular shape, or a U-shape as well. Further, the entirety (base end part) of one side of the film member 29 having the rectangular shape is fixed to the vicinity of the hole 28 and the other side (free end part) of the film member 29 is structured to be rolled-up so as to be turned away from the hole 28. In this structure, it is preferable that this rolled-up part has the same width as that of the fixed side of the film member 29 or a narrower width than that of the fixed side of the film member 29. By doing so, it is possible to close the hole 28 with the film member 29 in a stable manner.

It is to be noted that in the first embodiment noted above, the rigidity of the opening means 15 is such a rigidity that it does not bend beyond the projecting length L of the ridges 21, so that the entry prevention means of the first embodiment is constituted. However, the entry prevention means may also be configured in other modes. For example, a convex part extending from a part of the inner peripheral surface of the frame 14 toward the opening means 15 is provided, and when the opening means 15 is in the normal position, the opening means 15 will not contact the convex part, and when the opening means 15 is pushed in and moved by a predetermined entry length, the opening means 15 may come into contact with this convex part to prevent the opening means 15 from further entering, thereby creating the entry prevention means.

It is to be noted that the pre-filled syringe 1 of the first embodiment can be used as a simple syringe to be used at the time of a disaster or emergency situation. In addition, in the pre-filled syringe 1, there is no chance for the chemical solution to come into contact with the outside air, so that the chemical solution will not be contaminated. Furthermore, since the time length from the opening of the injection needle to the actual use of the injection needle can be shortened, the possibility that the injection needle 2 is exposed to the outside and contaminated can be reduced. In particular, the convenience when using the pre-filled syringe 1 in the open air is improved.

[Second Embodiment]

Next, a sealing container according to the second embodiment of the present invention will be described with reference to FIGS. 17 to 21. Reference numeral 40 in FIG. 17 denotes a pouch type pack as the sealing container of the second embodiment. The pouch type pack 40 is a disposable packaging member provided in the market in a state that a beverage (content) is pre-filled.

Figure 17:
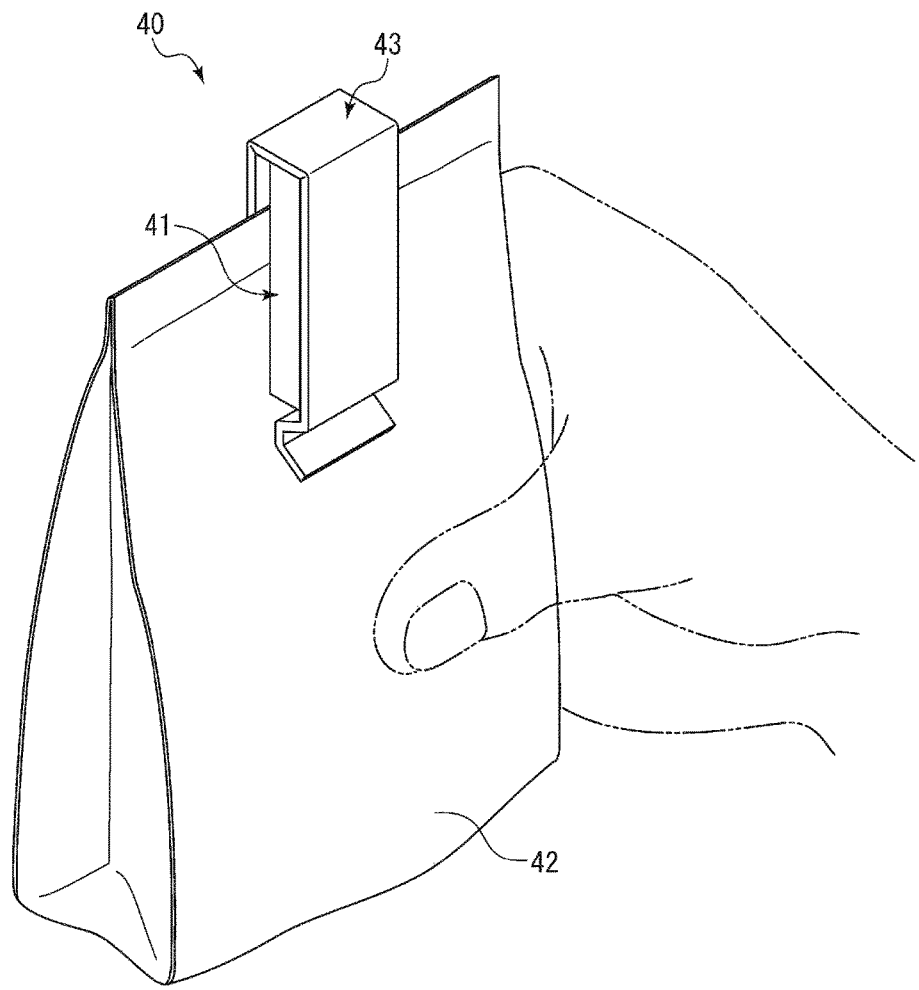
FIG. 17 is a perspective view showing a pouch type pack as a sealing container of the second embodiment of the present invention.

As shown in FIG. 17, the pouch type pack 40 includes a spout unit 41 (discharge pipe) which can be put into a mouth of a user and a bag-shaped member 42 (accommodating unit: a member forming an accommodating space) forming a bag-like shape filled with the beverage therein, and a plate-shaped member 43 (plate member) having a rectangular plate shape. The pouch type pack 40 is provided in a state where the spout unit 41 is covered with the plate-shaped member 43 which is bent. Further, the bag-shaped member 42 is formed on the basis of a sheet obtained by laminating a synthetic resin film, an aluminum foil or the like by a lamination process.

Figure 18:
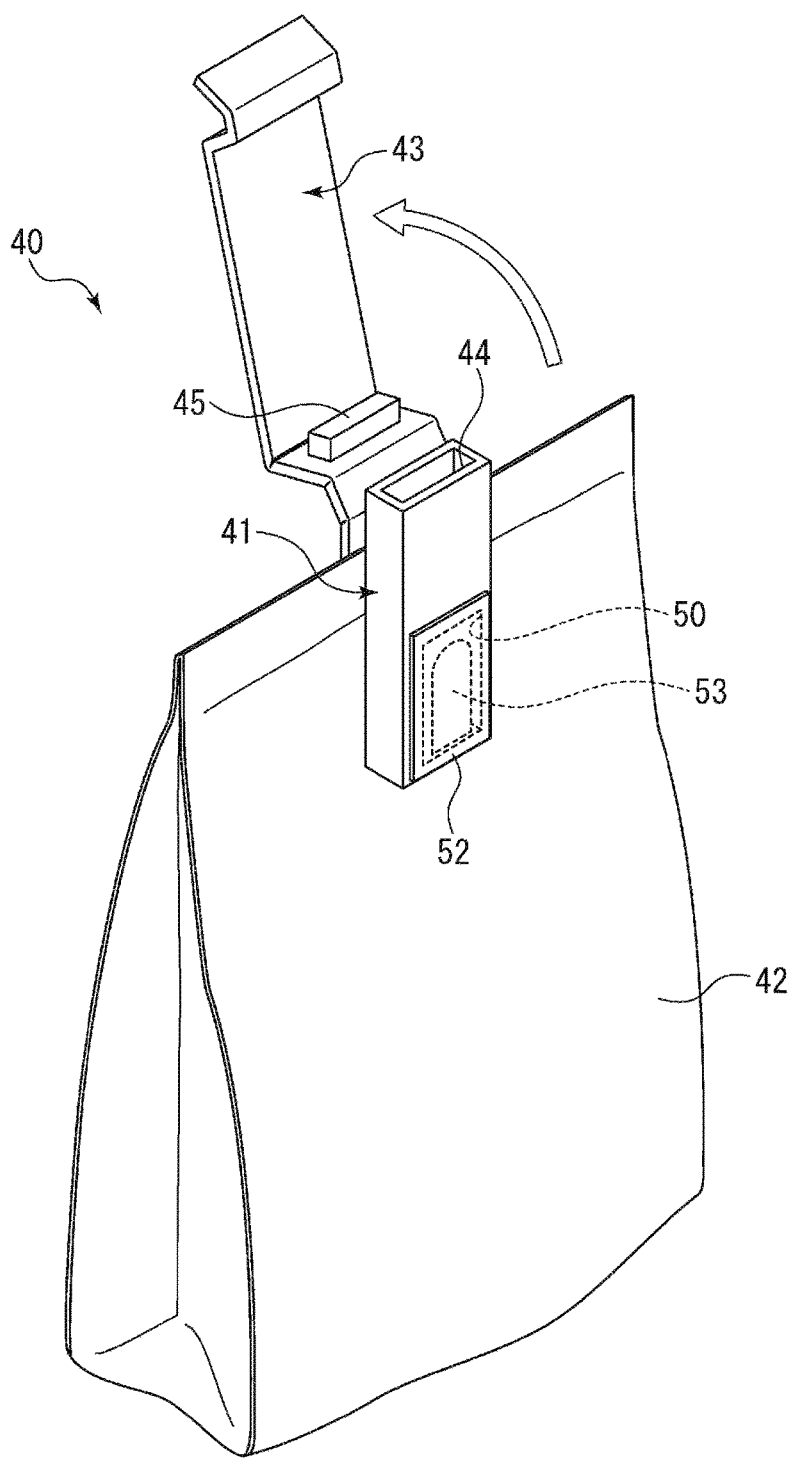
FIG. 18 is a perspective view showing a state in which a cover plate portion of the pouch type pack is opened.

As shown in FIG. 18, the spout unit 41 is a rectangular parallelepiped provided on the upper part of the bag-shaped member 42. A drinking port 44 (ejection port) is provided on the tip (upper surface) of the spout unit 41. Since this drinking port 44 has a horizontally elongated quadrangular shape, the user is easy to put it into the mouth. In the bag-shaped member 42 shown in FIGS. 17 to 21, in the following description, the side on which the spout unit 41 is provided will be referred to as a front surface side, and the side opposite to the front surface side will be referred to as a rear surface side.

As shown in FIGS. 17 and 18, the plate-shaped member 43 is attached to the upper part of the bag-shaped member 42 corresponding to the spout unit 41. The lateral width dimension of the plate-shaped member 43 is substantially the same as the lateral width dimension of the spout unit 41. The length dimension of the plate-shaped member 43 is longer than that of the spout unit 41. Further, a plurality of bent portions are provided in the longitudinal direction of the plate-shaped member 43 so that the plate-shaped member 43 can be bent. In this structure, by bending the plurality of bent portions of the plate-shaped member 43, the spout unit 41 can be covered by the plate-shaped member 43 from the rear surface side to the front surface side.

Figure 19:
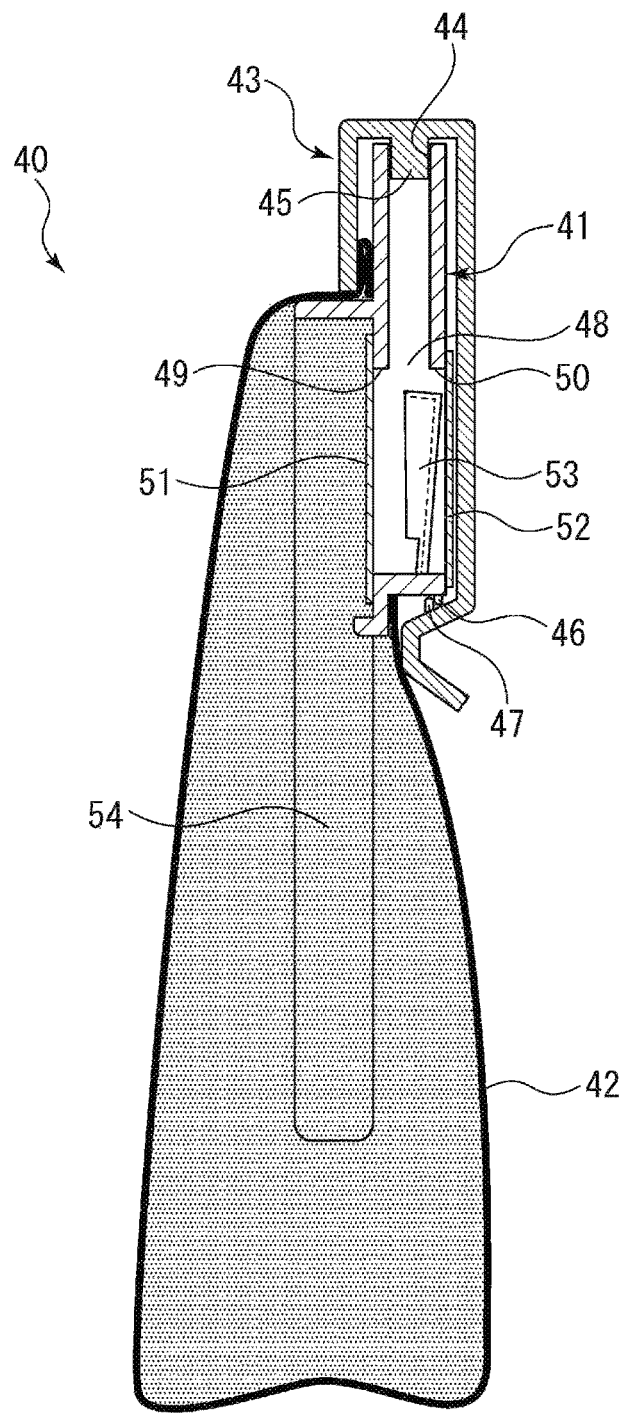
FIG. 19 is a side cross-sectional view showing the pouch type pack.

As shown in FIG. 19, the plate-shaped member 43 can cover the rear surface side, the upper surface side, and the front surface side of the spout unit 41, respectively. A block-shaped plug 45 configured to be capable of closing the drinking port 44 on the upper surface of the spout unit 41 is provided on the back surface side of the plate-shaped member 43.

Further, a hooking unit 47 to be hooked to a latching unit 46 provided at the lower part of the spout unit 41 is formed in the vicinity of the distal end of the plate-shaped member 43. Further, the distal end part of the plate-shaped member 43 is bent in a manner to form a V shape in a side view, so that a user can hook a finger to the distal end (tip). When the user removes the plate-shaped member 43 from the spout unit 41, the tip of the plate-shaped member 43 is elastically deformed by hooking the tip of the plate-shaped member 43 by the user's finger, so that the hooking unit 47 can be removed from the latching unit 46 on the spout unit 41. Further, when the user swings the plate-shaped member 43, the plug 45 is disengaged from the drinking port 44 of the spout unit 41, and thus, the plate-shaped member 43 is separated (opened) from the spout unit 41 (see FIG. 18).

In addition, a cavity is formed inside the spout unit 41 which has a box shape. This cavity constitutes a front chamber 48 of the second embodiment. The front chamber 48 can be opened to the outside through the drinking port 44 (see FIG. 20). Further, a first opening unit 49 is formed on the rear surface side of the lower part of the spout unit 41. Further, a second opening unit 50 is formed on the front surface side of the lower part of the spout unit 41. The first opening unit 49 and the second opening unit 50 are formed at the positions that are facing each other. In addition, both of the first opening 49 and the second opening 50 are square (rectangular) openings having the same vertical and horizontal widths (see FIG. 18).

It is to be noted that the first opening unit 49 is a part that is opened toward the inside of the bag-shaped member 42. The first opening unit 49 is closed by the sealing film 51 from the inner side of the bag-shaped member 42. It is to be noted that the whole peripheral edge of the sealing film 51 is adhered to the peripheral edge (spout unit 41) of the first opening unit 49. Further, the beverage filled in the inside of the bag-shaped member 42 is maintained in a state sealed by the sealing film 51. Further, the sealing film 51 is formed on the basis of a sheet obtained by laminating a synthetic resin film, an aluminum foil or the like by a lamination process.

It is to be noted that the second opening unit 50 is a part that is opened toward the outside. The second opening unit 50 is closed by an operation film 52 from the outside of the spout unit 41. It is to be noted that the whole peripheral edge of the operation film 52 is adhered to the peripheral edge (spout unit 41) of the second opening unit 50. Further, the second opening unit 50 closed by the operation film 52 constitutes the operation unit of the second embodiment. Further, the operation film 52 is formed of a material such as a synthetic resin which is easily elastically deformed. Further, the plate-shaped member 43 is configured to be able to cover the second opening unit 50 provided with the operation film 52. This plate-shaped member 43 constitutes a protection means for protecting the operation film 52 from being subjected to an external force.

In the front chamber 48 of the spout unit 41, an opening means 53 is provided. The opening means 53 is a thin plate-like protruding piece whose edge on the tip side (upper end side) thereof is rounded in a semicircular shape (see FIG. 18). The opening means 53 extends upward from the bottom surface in the front chamber 48 of the spout unit 41. In addition, the opening means 53 is separated from the other inner surfaces of the spout unit 41. Further, the opening means 53 is configured to be capable of swinging back and forth with the base end side (lower end side) as a fulcrum. That is, although the opening means 53 is formed integrally with the plate-shaped member 43, it is elastically deformable because the opening means 53 has a thin plate shape.

It is to be noted that the sealing film 51 and the operation film 52 are disposed so as to be parallel to each other in a side view. Further, the opening means 53 is disposed between the sealing film 51 and the operation film 52. In addition, the opening means 53 is disposed in an inclined manner so that its distal end side is close to the operation film 52. That is, the opening means 53 is inclined so that its leading end side is away from the sealing film 51, thus, the sealing film 51 and the operating film 52 and the opening means 53 are not parallel in a side view.

In addition, the opening means 53 is provided with a blade which is projecting toward the sealing film 51. The blade has an acute shape and can penetrate the sealing film 51. The blade extends from the edge of the leading end of the opening means 53 to the edges of the side ends of the opening means 53. Accordingly, when the opening means 53 is pushed, the blade of the opening means 53 comes into contact with the sealing film 51, and a cut is formed in the sealing film 51 (see FIG. 20). It should be noted that the blade is formed in a U-shape (horseshoe shape) in a plan view similar to the blade of the first embodiment. As the blade passes through the sealing film 51, a U-shaped (horseshoe shape) cut (opening) is formed in the sealing film 51. In this way, by forming a U-shaped cut in the sealing film 51, it is possible to open the sealing film 51 without generating a cut-off piece in the sealing film 51.

Further, at the inside of the bag-shaped member 42, there is provided with an adhesion preventing unit 54 (space forming unit) for suppressing the close contact between the inner surfaces of the bag-shaped members 42. The adhesion preventing unit 54 is a part integrally formed with the spout unit 41, and is constituted by two plate-shaped units extending rearward from the rear surface side of the spout unit 41 and extending downward. These two plate-shaped units are arranged in parallel to each other, and the first opening unit 49 is arranged between them. By providing the adhesion preventing unit 54 in this manner, the inner surface of the bag-shaped member 42 is prevented from approaching (contacting) the sealing film 51 (the first opening unit 49). As a result, a sufficient space is created for ensuring the penetration length for the blade of the opening means 53 to enter the inside of the bag-shaped member 42 beyond the sealing film 51 which is at the normal position (non-bulging position) from the outside of the bag-shaped member 42.

Figure 20:
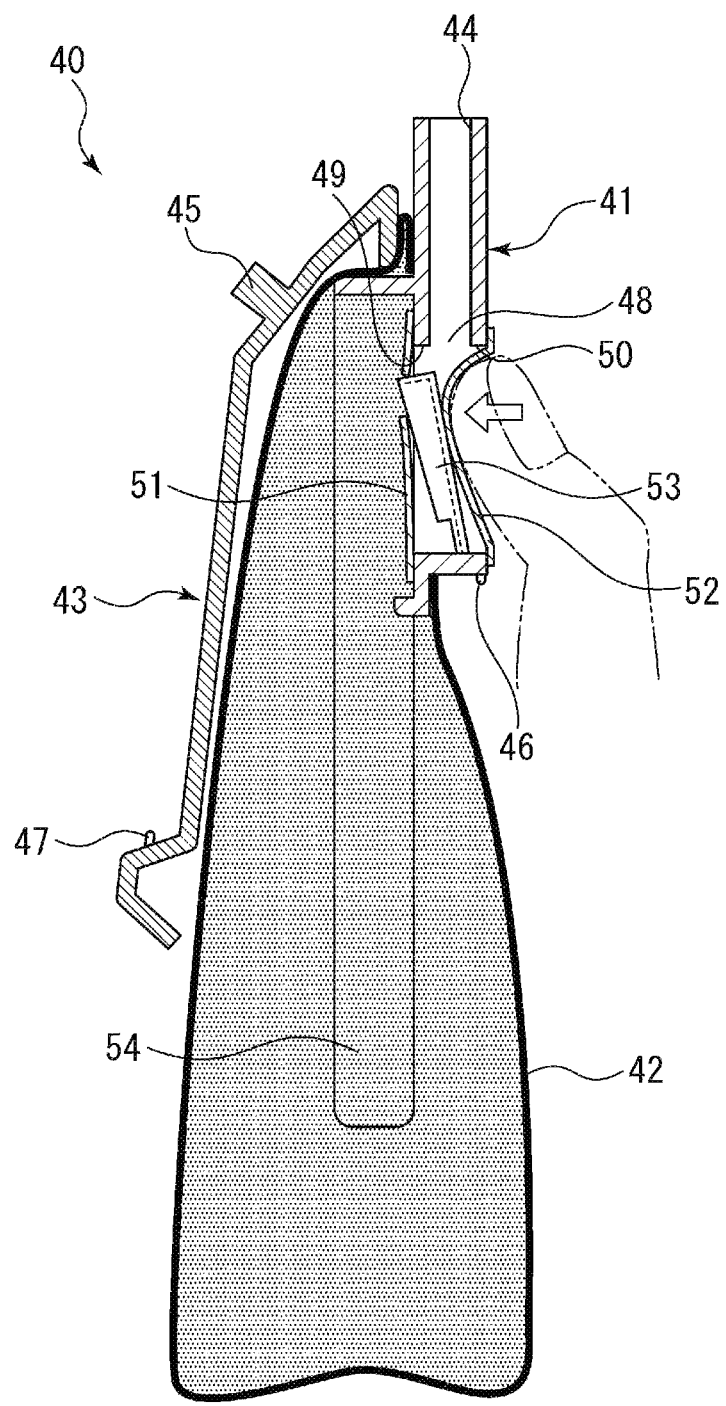
FIG. 20 is a side cross-sectional view showing the pouch type pack during an opening operation conducted by a user.

As shown in FIGS. 18 and 20, when the user removes the plate-shaped member 43 from the spout unit 41, the operation film 52 is exposed as well as the plug 45 is detached from the drinking port 44. In this state, when the user pushes the operation film 52 with the thumb, the opening means 53 is moved from the normal position toward the sealing film 51, the blade passes through the sealing film 51, and as a result, the sealing film 51 is opened. When the sealing film 51 is opened, the beverage in the bag-shaped member 42 can flow out into the front chamber 48.

Figure 21:
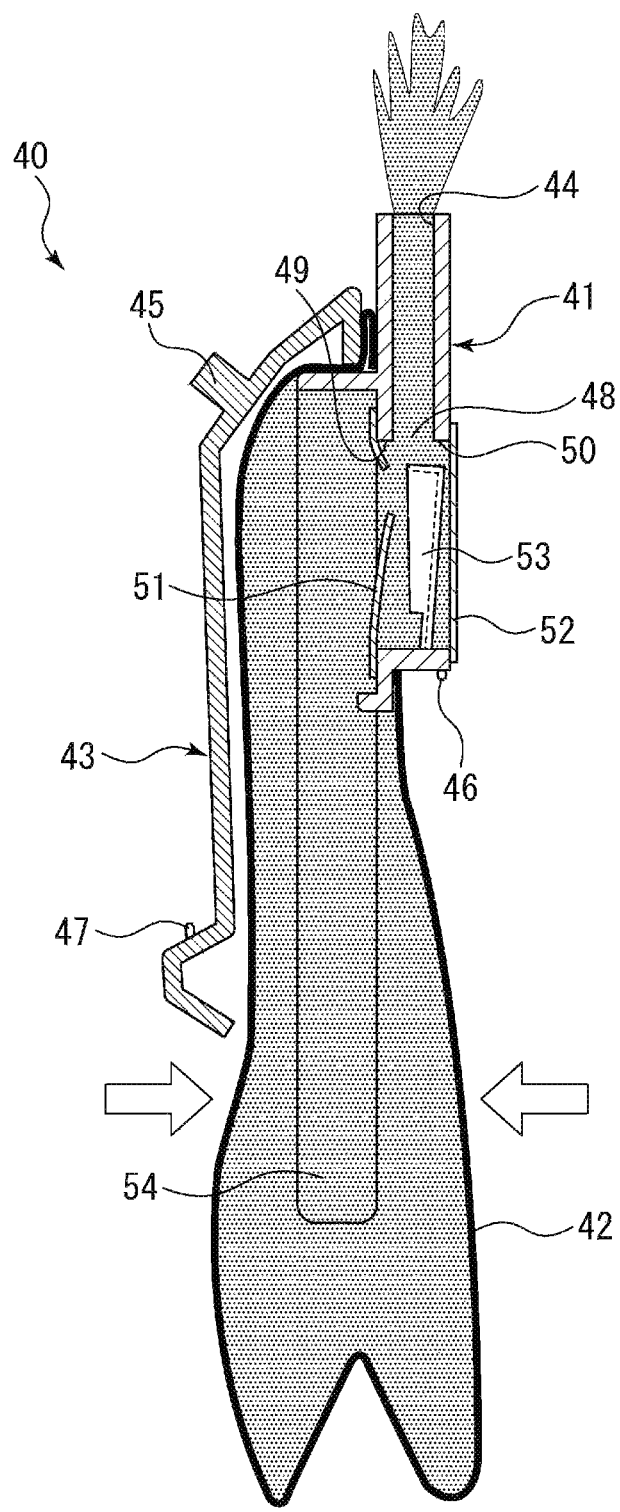
FIG. 21 is a side cross-sectional view showing a use state of the pouch type pack.

When the user releases the thumb from the operation film 52, the opening means 53 returns to the normal position (retracted position) separated from the sealing film 51 by its elastic force (see FIG. 21). Therefore, the opening means 53 is separated from the opening formed in the sealing film 51, so that the opening means 53 will not prevent the beverage in the bag-shaped member 42 from being discharged into the front chamber 48. It is to be noted that a unit in which the opening means 53 has an elastic force and can return to the normal position constitutes the moving means of the second embodiment.

It is to be noted that since the operation film 52 (confirmation means) is a transparent member, the user is able to confirm whether or not the beverage can flow out into the front chamber 48 by monitoring the front chamber via the operation film 52. That is, it is possible for the user to visually confirm via the operation film 52 that the sealing film 51 is opened, and thus, it has become possible to drink the beverage.

As shown in FIG. 21, when the user grips the bag-shaped member 42 having flexibility after opening the sealing film 51, the pressure of the beverage in the bag-shaped member 42 is increased, and the beverage is discharged from the opening of the sealing film 51 into the front chamber 48 and then flows out from the drinking port 44 of the spout unit 41. Further, the user can suck out the beverage inside the bag-shaped member 42 by holding the drinking port 44 in the mouth. It is to be noted that when the user sucks out the beverage, the inner surface of the bag-shaped member 42 is prevented from being brought into close contact with each other by the adhesion preventing unit 54 inside the bag-shaped member 42, so that the user can consistently suck out the beverage stored inside the bag-shaped member 42.

After drinking the beverage inside the bag-shaped member 42, the plate-shaped member 43 can be pivoted to attach the plate-shaped member 43 to the spout unit 41 again. At this time, the drinking port 44 of the spout unit 41 is closed again by the plug 45 of the plate-shaped member 43. Therefore, even if there is the beverage remained inside the bag-shaped member 42, the beverage will not spill out from the drinking port 44. Further, it is also possible to open the sealing film 51 in a state in which the drinking port 44 is closed by the plug 45, and thereafter to remove the plug 45 from the drinking port 44. By doing so, it is possible to prevent the beverage inside the bag-shaped member 42 from being ejected at the same time with opening of the sealing film 51. Further, it is possible that the plate-shaped member 43 is made of synthetic resin or the like, and the plug 45 is made of a material such as elastomer which is easily elastically deformed, so that the plate-shaped member 43 and the plug 45 can be integrally formed by a two-color molding (different material forming) process.

As described above, in the pouch-type pack 40 of the second embodiment of the present invention, the user pushes the operation film 52 so that the opening means 53 penetrates the sealing film 51. In this arrangement, it is possible to discharge the beverage from the bag-shaped member 42 at a timing different from the timing at which the sealing film 51 is pierced by the opening means 53. Thus, the user can perform only the operation of opening the sealing film 51, so that the user can arbitrarily select the timing at which the beverage is discharged. In the second embodiment, the bag-shaped member 42 constitutes the discharge means in that a pressure is externally applied thereto or the user sucks out so that the bag-shaped member 42 becomes capable of discharging the fluid stored inside.

It is to be noted that, with respect to the spout pouch pack in the conventional technology using a screw cap, when the contents therein include extremely small low molecules (hydrogen or the like), there arises a possibility that these low molecules leak out from the screw cap. In the pouch type pack 40 of the second embodiment, however, since the first opening 49 is closed by the sealing film 51 and as a result, high airtightness is maintained, even if the contents include the extremely small low molecules which tend to leak out, such contents can be maintained in the pouch type pack for a long period of time. In addition, if it is attempted to enhance the sealing performance by using the screw cap in the conventional spout pouch pack, the screw cap must be firmly tightened, which makes opening the pack difficult, however, in the pouch-type pack 40 of the second embodiment, the sealing property can be enhanced while it can be easily opened.

It is to be noted that the pouch type pack 40 of the second embodiment noted above need not be a one that has to be operated by human fingers, but it is possible that the pouch type pack 40 is used as a component (cartridge) detachably mounted on a predetermined apparatus.

[Third Embodiment]

Figure 22:
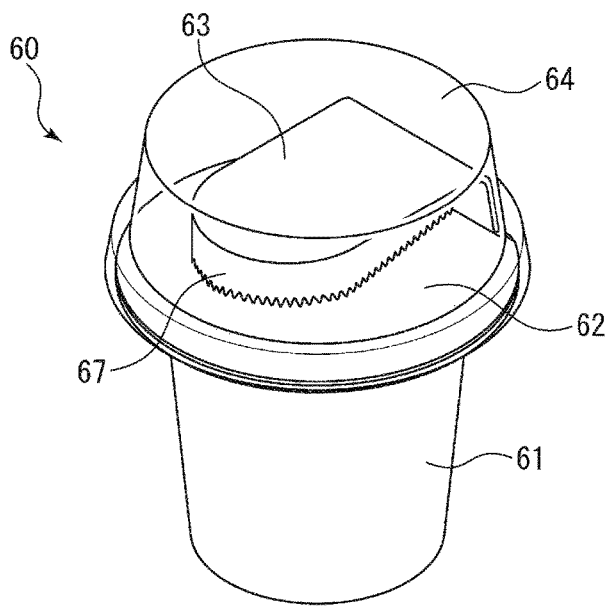
FIG. 22 is a perspective view showing a single-serving container as a sealing container of the third embodiment of the present invention.

Next, a sealing container according to the third embodiment will be described with reference to FIGS. 22 to 28. In FIG. 22, reference numeral 60 denotes a single-serving container (a potion type container) as a sealing container of the third embodiment. This single-serving container 60 is a small cup container which is provided in the market in a state in which beverages (contents) such as cream (dairy product) and gum syrup to be added to coffee, tea, and the like are pre-filled.

Figure 26:
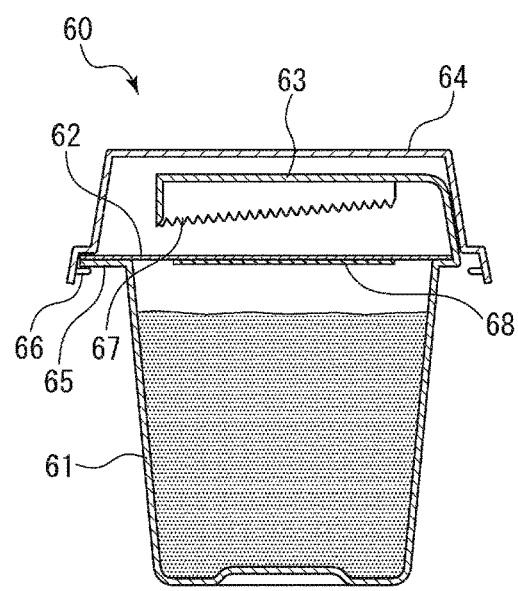
FIG. 26 is a side cross-sectional view showing the single-serving container.

As shown in FIGS. 22 and 26, the single-serving container 60 includes, as main components, a cup 61 (accommodating unit: a member forming an accommodating space) forming a cup shape (bottomed cylindrical shape) for containing a beverage therein, a sealing film 62 for airtightly closing an upper opening of the cup 61, an opening means 63 extending upward from one end of the cup 61 and provided close to the sealing film 62, a lid member 64 (protective means) for covering the sealing film 62 and the opening means 63. The sealing film 62 is formed on the basis of a sheet obtained by laminating a synthetic resin film, an aluminum foil or the like by a lamination process. In addition, the cup 61 is made of a material such as an opaque synthetic resin. Further, the lid member 64 is made of a material such as a transparent synthetic resin.

Figure 25:
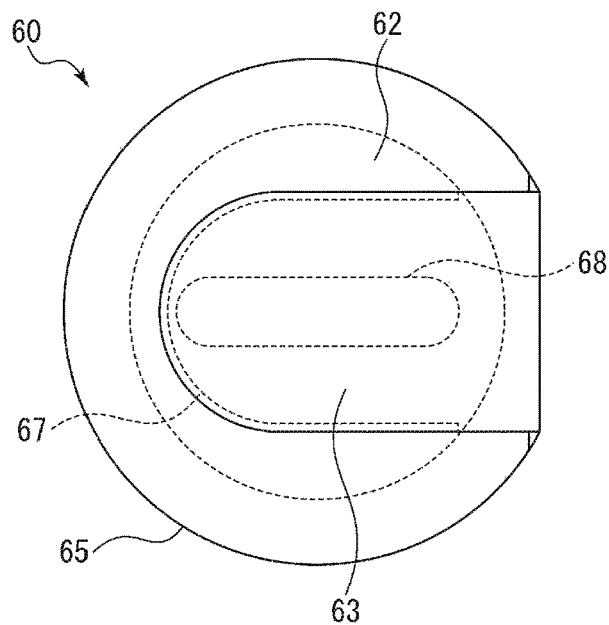
FIG. 25 is a plan view showing the single-serving container.

As shown in FIG. 25, the cup 61 has a circular shape in a plan view. The peripheral edge of the sealing film 62 is adhered to a peripheral piece 65 around the opening of the cup 61, whereby the sealing film 62 airtightly seals the inside of the cup 61. Further, the lid member 64 has a circular shape in a plan view corresponding to the peripheral piece 65 of the cup 61. By covering the sealing film 62 and the opening means 63 with the lid member 64, when an unnecessary external force is applied to the single-serving container 60 before use (during transportation), it is possible to prevent the sealing film 62 from being scratched or damaged by the opening means 63 when the opening means 63 is moved toward the sealing film 62. In addition, it is possible to prevent any other member from being scratched or damaged by being brought into contact with the sealing film 62.

On the inner surface side of the peripheral edge of the lid member 64, a latching strip 66 to be latched to the peripheral piece 65 of the cup 61 is provided in a projecting manner. It is to be noted that the latching strip 66 is provided over the entire length of the inner circumferential surface of the lid member 64. By detaching the latching strip 66 from the peripheral piece 65 of the cup 61, it becomes possible to separate the lid member 64 from the cup 61 (see FIG. 23).

It should be noted that the opening means 63 is a protruding piece having a thin plate shape in which the edge on the distal end side thereof is rounded in a semicircular shape. In addition, the opening means 63 extends upward from a part of the peripheral edge piece 65 of the cup 61 and is bent in an inverted L shape in a side view and is provided above the sealing film 62 (see FIG. 26). The opening means 63 is disposed so as to be parallel to the sealing film 62 in a side view. Further, the opening means 63 is configured to be capable of swinging in the vertical direction around the base end side as a fulcrum. It is to be noted that the flat surface of the opening means 63 constitutes the operating unit of the third embodiment. By pressing the upper surface of the opening means 63 with a finger by the user, the sealing film 62 can be opened (see FIGS. 23 and 27).

As shown in FIGS. 25 and 26, the opening means 63 is provided with a blade 67 that is downwardly projecting. The lower end edge of the blade 67 has a saw-tooth shape in which a plurality of protrusions are arranged. Thus, the sealing film 62 can be cut with this blade 67. The blade 67 extends from the edge of the leading end of the opening means 63 to the edge of each of the side ends. That is, the blade 67 is formed in a U-shape (horseshoe shape) in a plan view. At least a part (tip) of the blade 67 has a curve that matches the curved shape of the inner surface of the cup 61 in a plan view. As the blade 67 cuts the sealing film 62, a U-shaped (horseshoe shaped) cut (opening) is formed in the sealing film 62.

It is to be noted that the blade 67 of the third embodiment may not be formed as a sharp blade that can completely penetrate the sealing film 62. For example, it is also possible that, when the user presses the opening means 63, the saw-tooth shaped blade 67 may come into contact with the sealing film 62 to form perforations in the sealing film 62. Further, when the user further pushes the sealing film 62 formed with perforations and the opening means 63 at the same time with the finger, the sealing film 62 is torn from the perforation, and thus, the sealing film 62 is opened.

Figure 23:
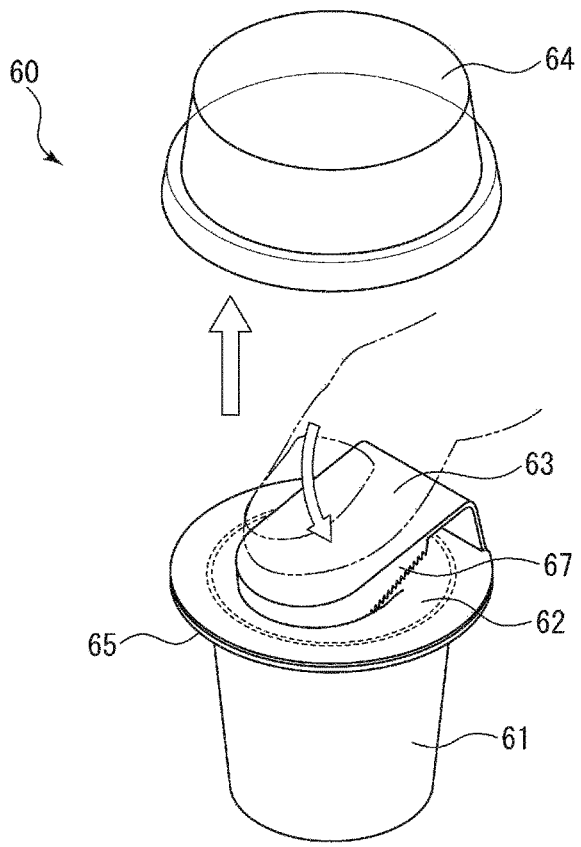
FIG. 23 is a perspective view showing the single-serving container during an opening operation conducted by a user.
Figure 24:
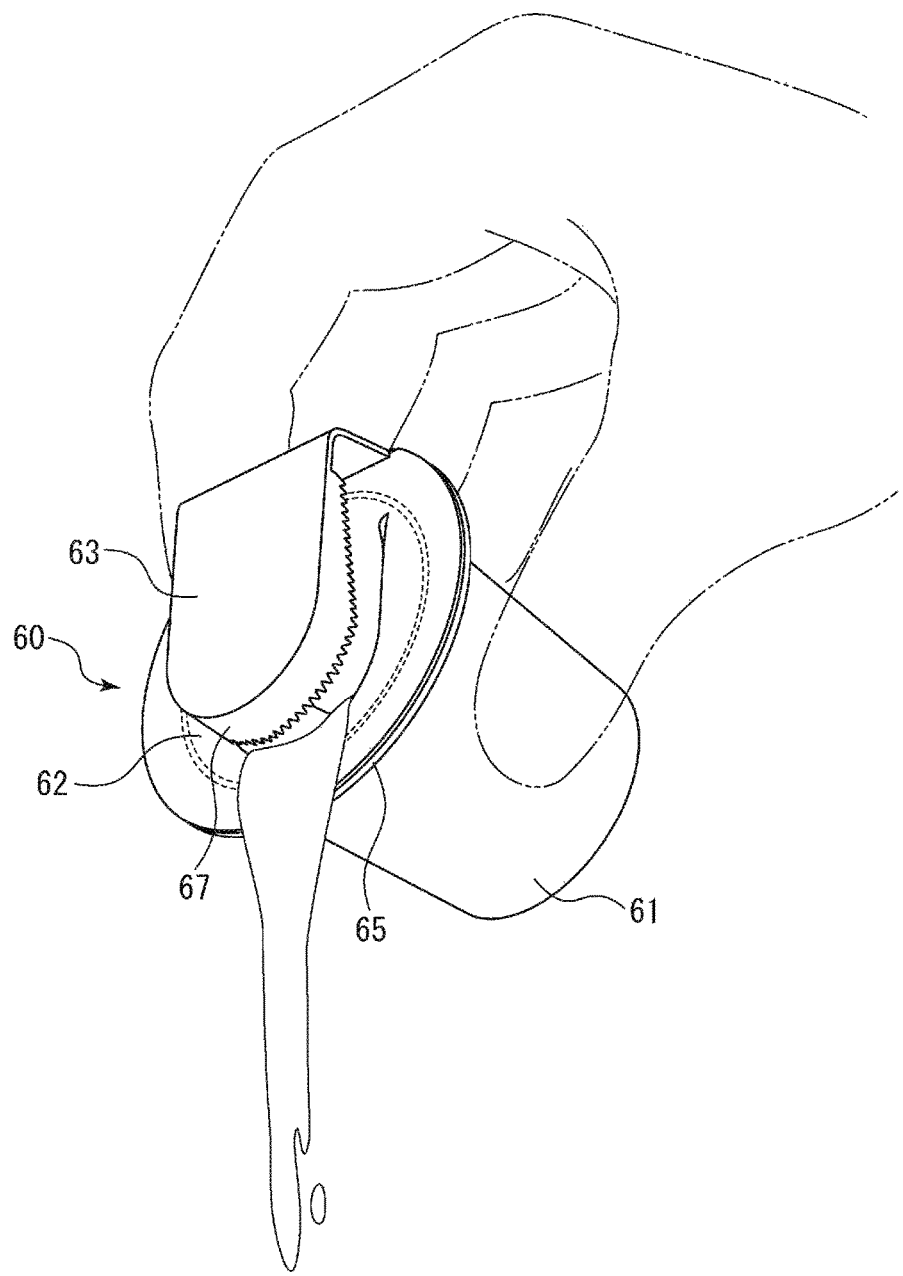
FIG. 24 is a perspective view showing a use state of the single-serving container.
Figure 27:
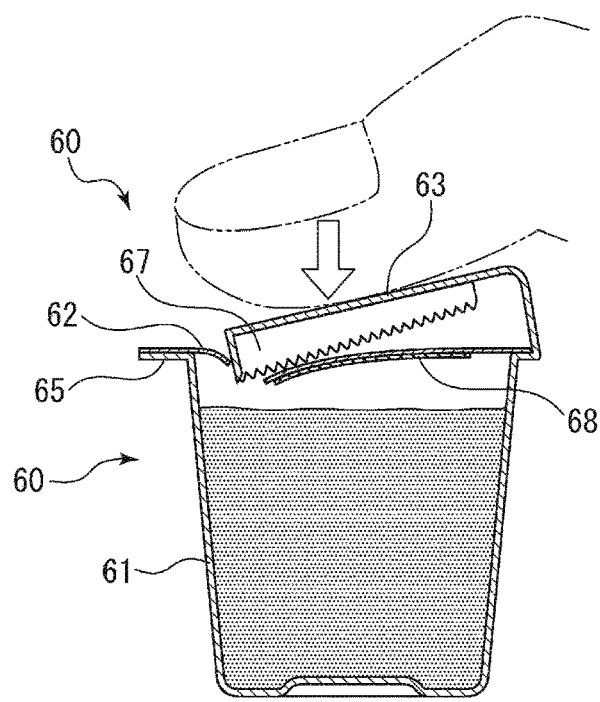
FIG. 27 is a side cross-sectional view showing the single-serving container during the opening operation conducted by the user.

As shown in FIGS. 23 and 27, when the user removes the lid member 64 from the cup 61, the opening means 63 and the sealing film 62 are exposed. In this state, when the user pushes the upper surface of the opening means 63 with the thumb, the opening means 63 is moved from the normal position toward the sealing film 62, and the blade 67 cuts the sealing film 62, thereby opening the sealing film 62. In other words, the blade 67 exceeds the sealing film 62 which is at the normal position, whereby the sealing film 62 is opened. When the sealing film 62 is opened, the beverage can be discharged from the cup 61.

It is to be noted that in the third embodiment noted above, since the user can operate the opening means 63 in a state where the opening means 63 and the sealing film 62 can be visually recognized, it is possible for the user to grasp the timing at which the sealing film 62 is opened. In addition, since the user can perform the opening operation while directly touching the opening means 63, the user can grasp the timing at which the sealing film 62 is opened. As a result, the sealing film 62 will not be suddenly opened, and thus, there is no fear that the beverage inside the cup 61 will be scattered.

Figure 28:
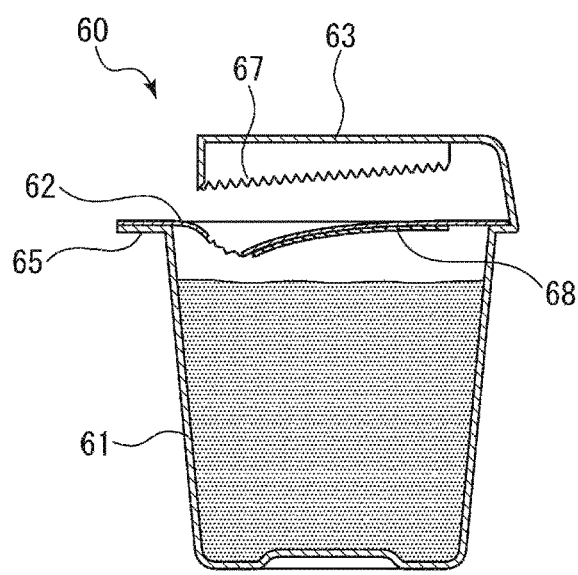
FIG. 28 is a side cross-sectional view showing the single-serving container after the opening operation.

When the user releases the thumb from the opening means 63, the opening means 63 returns to the normal position (retracted position) separated from the sealing film 62 by its elastic force (see FIG. 28). Therefore, the opening means 63 is separated from the opening formed in the sealing film 62, so that the opening means 63 does not prevent the beverage in the cup 61 from being discharged. It is to be noted that the unit in which the opening means 63 has the elastic force and can return to the normal position constitutes the moving means of the third embodiment. Then, when the single-serving container 60 is inclined in a state where the sealing film 62 is opened, the beverage inside the cup 61 is discharged (see FIG. 24). In addition, the user can arbitrarily adjust the timing at which the beverage is discharged. It is to be noted that at least a part of the cut is formed at a position close to the inner surface of the cup 61. Therefore, it is possible to discharge the beverage inside the cup 61 up to the last one drop.

It is to be noted that an auxiliary unit 68 (maintaining means) for maintaining the enlarged opening of the sealing film 62 with respect to the cut formed by the blade 67 is attached to the back surface of the sealing film 62 (see FIG. 25). Further, the auxiliary unit 68 is provided in the central part of the sealing film 62 so as not to come into contact with the U-shaped blade 67. The auxiliary unit 68 is a member formed of thick synthetic resin or the like, and is a member that maintains the bent state once it is bent.

As shown in FIG. 27, when the user pushes the sealing film 62 that is opened and the opening means 63 at the same time with the finger, the opening of the sealing film 62 is enlarged. The state in which the opening of the sealing film 62 is enlarged is maintained by the auxiliary unit 68. As a result, when the beverage inside the cup 61 flows out from the opening of the sealing film 62, the opening of the sealing film 62 will not be closed by the flow of the beverage, and thus, the beverage can be discharged smoothly.

It is to be noted that in the third embodiment noted above, the auxiliary unit 68 is a member different from the sealing film 62, however, the auxiliary unit 68 may be formed integrally with the sealing film 62. For example, the sealing film 62 itself may be made of a material that is able to maintain its bent state once it is bent. Further, it may also be configured such that the opening means 63 that has opened the sealing film 62 is prevented from returning to the normal position, and the state (shape) in which the opening means 63 is pushed is maintained, and as a result, the opening of the sealing film 62 is enlarged, thereby achieving the maintaining means for maintaining the open state.

It is to be noted that after the beverage inside the cup 61 is discharged, the lid member 64 is again attached to the cup 61 so as to cover the sealing film 62 and the opening means 63 with the lid member 64. In this way, even if there is a beverage remained inside the cup 61, the beverage will not spill out from the opening of the sealing film 62.

As has been described above, in the single-serving container 60 of the third embodiment of the present invention, since the sealing film 62 can be opened by using the opening means 63, it is possible for the user to easily open the single-serving container 60.

Further, since the opening means 63 is provided in a manner not to be separated from the cup 61, i.e., the opening means 63 is a member integrated with the cup 61, the opening means 63 is prevented from being lost. Further, the user can discard the opening means 63 as a member integrated with the cup 61 when discarding the used single-serving container 60.

[Fourth Embodiment]

Next, a sealing container according to the fourth embodiment of the present invention will be described with reference to FIGS. 29 to 33. It is to be noted that the same reference numerals are given to the same constituent parts as those shown in the third embodiment, and thus duplicate explanation regarding those parts will be omitted.

Figure 29:
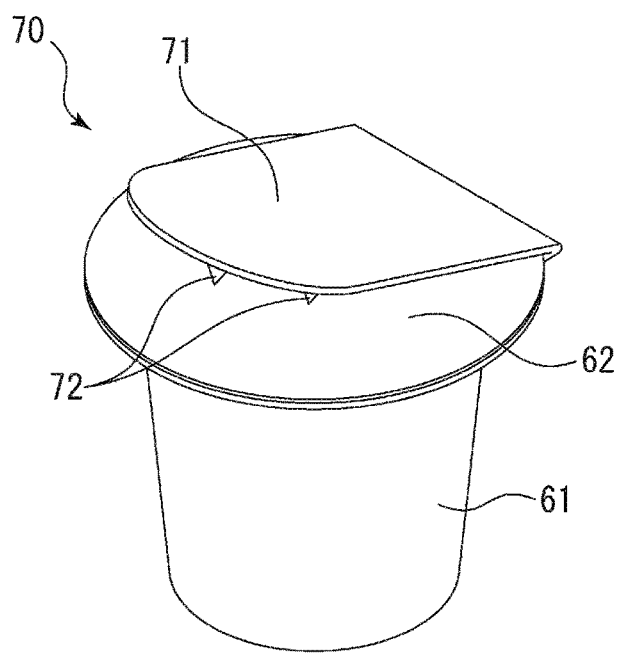
FIG. 29 is a perspective view showing a single-serving container as a sealing container of the fourth embodiment of the present invention.
Figure 30:
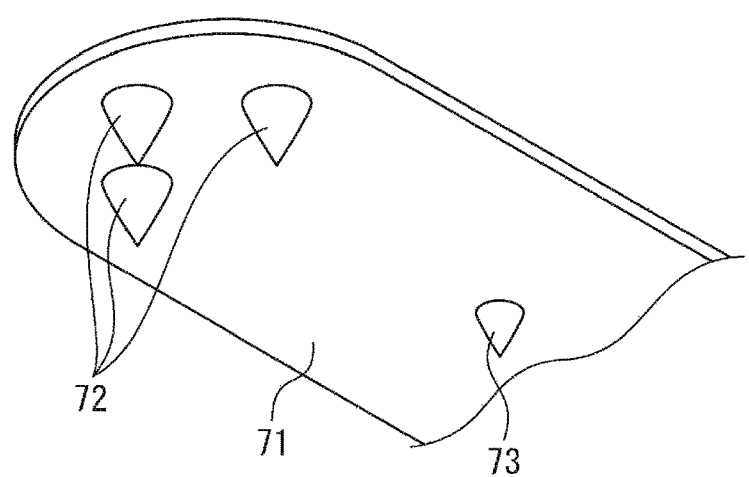
FIG. 30 is a perspective view showing an opening means of the single-serving container.
Figure 31:
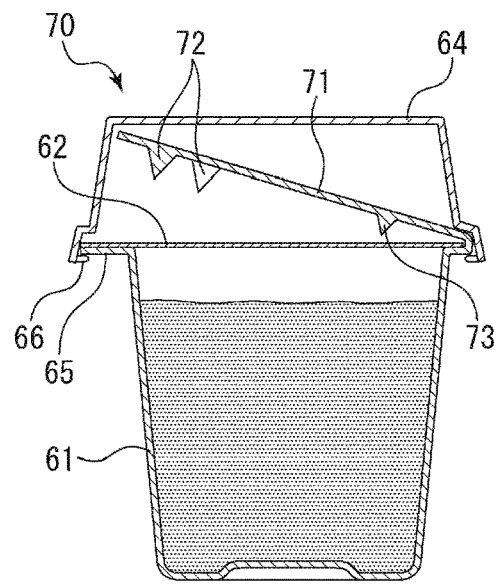
FIG. 31 is a side cross-sectional view showing the single-serving container.

As shown in FIGS. 29, 30, and 31, an opening means 71 of a single-serving container 70 as a sealing container of the fourth embodiment is inclined upward from a part of the peripheral piece 65 of the cup 61. Further, the opening means 71 is configured to be able to swing in the vertical direction with the base end side as a fulcrum. By pressing the upper surface of the opening means 71 with a finger by the user, the sealing film 62 can be opened (see FIG. 32).

In addition, the opening means 71 of the fourth embodiment is provided with three (plural) opening projections 72 each protruding downward. These opening protrusions 72 are arranged on the lower surface of the opening means 71 in a state where they are arranged on a curved line so as to be matched with the curved shape of the inner surface of the cup 61. Three (plural) discharge holes 74 (openings) are formed in the sealing film 62 by penetration of the opening projection 72 through the sealing film 62. These discharge holes 74 are formed along the curved shape of the inner surface of the cup 61 in a plan view. In addition to the discharge holes 74 formed in the sealing film 62, at a position distant from the opening projections 72, there is provided with one (single) air hole projection 73 (air hole forming means) for forming an air hole 75 for allowing the air to flow into the inside of the cup 61.

It is to be noted that the opening projections 72 are provided on the distal end side of the opening means 71. The air hole projection 73 is provided on the base end side of the opening means 71. Further, the opening means 71 is configured to be able to swing in the vertical direction with the base end side as a fulcrum. In addition, each of the opening protrusions 72 and the air hole protrusion 73 is formed in a conical shape whose lower end is acute. It is to be noted that the opening projection 72 and the air hole projection 73 are formed in a pyramidal shape or a rod shape. It is also possible that a larger number of opening protrusions 72 may be provided over the entire lower surface of the opening means 71, and a larger number of discharge holes 74 are formed throughout the entire sealing film 62 by these opening projections 72. Further, it is possible that the dimensions of the plurality of opening protrusions 72 are different from each other. Further, it is also possible to provide one (single) large opening projection 72.

Figure 32:
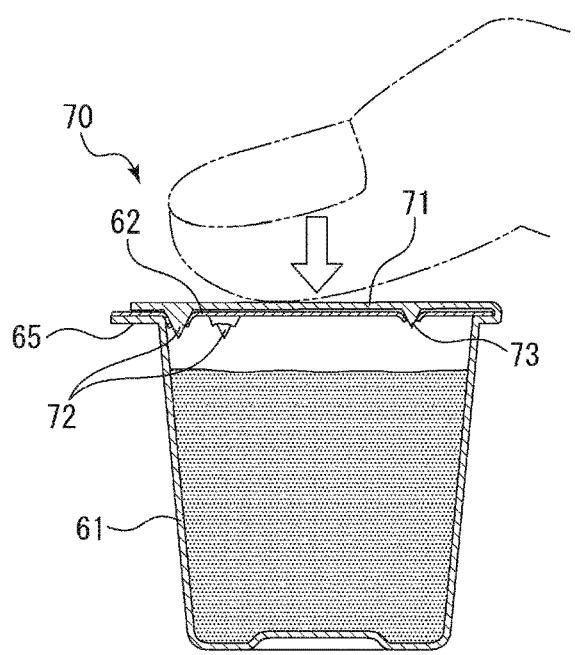
FIG. 32 is a side cross-sectional view showing the single-serving container during the opening operation conducted by the user.

As shown in FIG. 31, a lid member 64 (protective means) is provided for covering both the sealing film 62 and the opening means 71. As shown in FIG. 32, when the user removes the lid member 64 from the cup 61, the opening means 71 and the sealing film 62 are exposed. In this state, when the user pushes the upper surface of the opening means 71 with the thumb, the opening means 71 is moved from the normal position toward the sealing film 62, and at the time when the lower surface of the opening means 71 contacts the upper surface of the sealing film 62, the movement of the opening means 71 is stopped. It is to be noted that, also, when the tip end of the opening means 71 hits (hooks) the peripheral edge piece 65 of the cup 61, the movement of the opening means 71 is stopped. In this state, the opening projections 72 and the air hole projection 73 penetrate the sealing film 62. In other words, the opening projections 72 and the air hole projection 73 exceed the sealing film 62 that is at the normal position, whereby the sealing film 62 is opened. In this manner, the discharge hole 74 (first opening) and the air hole 75 (second opening) are formed in the sealing film 62 (see FIG. 33). It should be noted that the lower surface of the opening means 71 is brought into contact with the upper surface of the sealing film 62 or the distal end of the opening means 71 hits the peripheral piece 65 of the cup 61 so that the opening means 71 can no longer be moved downward, thereby constituting the entry prevention means of the fourth embodiment. Furthermore, when the sealing film 62 is opened, the upper surface of the sealing film 62 is covered with the opening means 71, so that the beverage will not be scattered around. It is to be noted that the swinging fulcrum of the opening means 71 is provided at a position substantially the same height as the position of the sealing film 62. As a result, the entire lower surface of the opening means 71 can be brought into close contact with the upper surface of the sealing film 62.

Figure 33:
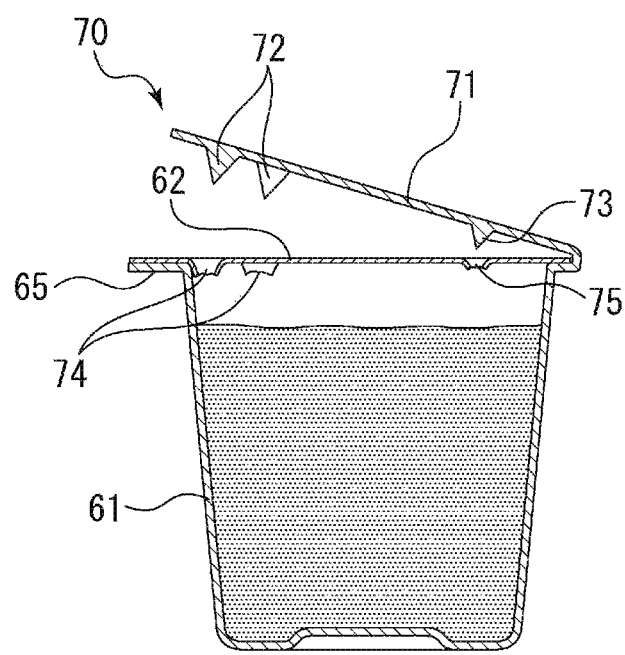
FIG. 33 is a side cross-sectional view showing the single-serving container after the opening operation.

Further, when the user releases the thumb from the opening means 71, by its elastic force, the opening means 71 returns to the normal position (retracted position) separated from the sealing film 62 (see FIG. 33). In this state, since the opening means 71 is separated from the discharge holes 74 and the air hole 75 formed in the sealing film 62, the beverage in the cup 61 is discharged from the discharge holes 74 without being prevented from flowing out, and the air is not prevented from flowing into the cup 61 via the air hole 75. It is to be noted that a unit in which the opening means 71 has an elastic force and can return to the normal position constitutes the moving means of the fourth embodiment. Then, when the single-serving container 70 is inclined in a state where the sealing film 62 is opened, the beverage inside the cup 61 is discharged from the discharge holes 74. In addition, the user can arbitrarily adjust the timing at which the beverage is discharged. It is to be noted that the discharge holes 74 are formed at a position close to the inner surface of the cup 61 in a plan view. As a result, it is possible to discharge the beverage inside the cup 61 completely up to the last one drop. Further, the air hole 75 is provided at a position away from the position of the discharge holes 74 with respect to the central part of the cup 61. Therefore, when the cup 61 is inclined so that the beverage is discharged from the discharge holes 74, there is no possibility that the air hole 75 is blocked by the beverage.

As described above, in the single-serving container 70 of the fourth embodiment noted above, since the air hole 75 is formed in the sealing film 62, when the beverage in the cup 61 is discharged from the discharge holes 74 formed in the sealing film 62, the air can flow into the cup 61 from the air hole 75, so that the beverage can be discharged smoothly from the cup 61. In particular, when the content is composed of a viscous liquid such as cream or gum syrup, there arises a possibility that a liquid film may be formed at the discharge holes 74 when discharging the beverage from the discharge holes 74. In the fourth embodiment, however, since the air hole 75 is formed separately from the discharge holes 74, even if such a liquid film is formed in the discharge holes 74, the air can easily flow into the cup 61.

Further, the air hole projection 73 is provided so as to be movable toward the sealing film 62 together with the movement of the opening means 71. As a result, when the sealing film 62 is opened by using the opening means 71, the air hole 75 can be formed at the same time. Thus, it is possible for the user to easily form the air hole 75 in the sealing film 62.

In the third embodiment as well as in the fourth embodiments, the liquid beverages such as cream (milk drink) and gum syrup are contained in the single-serving containers 60 and 70, however, fluidly moving beverages of powdery material (powder) such as sugar, salt, pepper and the like may also be contained in the single-serving containers 60 and 70. In addition, contents other than food and drink such as a mouth wash may also be contained in the single-serving containers 60 and 70.

Although the sealing containers according to the present invention have been described based on the first to fourth embodiments, the same effect can be obtained even if the configuration applied in any one of the above noted embodiments is applied to other embodiments. Further, the configurations applied in each of the embodiments may be combined with one another. For example, the opening means 71 having the opening projection 72 of the fourth embodiment may be applied to the opening means 15 and 53 of the first embodiment and the second embodiment. Within the context of the present invention the term "means" may also be referred to as "part", "mechanism", "element", or the like.

It is to be noted that the sealing container of the present invention does not need to have a high level of airtightness as long as it is a container that can be maintained in a sealed state so as not to leak the contents of the container. Thus, substances (for example, air, etc.) other than the intended contents may be able to pass between the interior and the exterior of the sealing container. For example, the bag-shaped members 3 and 42 of the above-described embodiments may have minute holes through which the air or the like can pass.

It is to be noted that the sealing container of the present invention is used to accommodate a liquid medicine or a beverage as a liquid (fluid) content, but the sealing container of the present invention may also be used as a container to accommodate a liquid seasoning such as ketchup or sauce, or chemicals such as a paint, a detergent, an adhesive or the like. Also, the content of the present invention is not limited to liquid, but may be gas or powdery substance (powder) as long as it is a substance that is fluidly movable.

INDUSTRIAL APPLICABILITY

The sealing containers of the present invention can be applied not only to containers for food packaging, medical instruments, daily necessaries, but also can be applied to other industrial products.

EXPLANATION OF REFERENCE NUMERALS

1: pre-filled syringe, 2: injection needle, 3: bag-shaped member, 4: plate-shaped member, 40: pouch type pack, 41: spout unit, 42: bag-shaped member, 43: plate-shaped member, 60: single-serving container, 61: cup.

What is claimed is:

1. A sealing container, comprising:
   a bag-shaped member for accommodating contents therein,
   a sealing film for sealing the bag-shaped member,
   an opening means so configured that at least a part of which is movable by being pushed toward the sealing film and is capable of opening the sealing film,
   an operation unit configured to be capable of conducting an operation to move the opening means,
   a front chamber into which the contents discharged from the opening formed in the sealing film by the opening means enter,
   a discharge pipe having a discharge port for discharging the contents outward from the front chamber,
   a plate-shaped member to which the bag-shaped member is attached and is configured to be bendable, and
   a protection means that is provided on the plate-shaped member and is configured to cover the operation unit when the plate-shaped member is bent to be in a transporting state,
   wherein when the plate-shaped member is bent to be in a use state, which is by being bent in an opposite direction from the transporting state, the protection means is separated from the operation unit for conducting the operation to move the opening means, and the plate-shaped member sandwiches at least a part of the bag-shaped member when the plate-shaped member is bent to raise a pressure of the contents and to discharge the contents from the bag-shaped member.

2. The sealing container as defined in claim 1, further comprising:
   a moving means for moving at least a part of the opening means penetrating the sealing film toward a direction to separate the part of the opening means from the sealing film.

3. The sealing container as defined in claim 1, further comprising:
   a space forming unit which forms a space inside the bag-shaped member to secure an entering length by which the opening means enters the bag-shaped member when the opening means penetrates through the sealing film and to prevent the opening means from coming into contact with an inner surface of the bag-shaped member.

4. The sealing container as defined in claim 1, wherein the opening means has a linearly shaped blade at least a part of which is bent and a cut is formed in the sealing film by the blade.

5. The sealing container as defined in claim 1, further comprising:
   a confirmation means configured to be capable of allowing the user to confirm that the contents have entered the front chamber.

6. The sealing container as defined in claim 1, further comprising:
   a check valve means for preventing reverse flow of the contents that are flowing from the front chamber toward the discharge port.

7. The sealing container as defined in claim 1, wherein the front chamber is formed by the sealing film and an operation film which is disposed to face the sealing film to be parallel with each other when viewed from a side and covers the opening means in such a state where the opening means can be operable.

8. The sealing container as defined in claim 1, further comprising:
   a storage means which is provided to the plate-shaped member so as to be capable of swinging with respect to the discharge pipe and is configured to be capable of storing at least a part of the discharge pipe when the plate-shaped member is bent to be in the transporting state.

9. The sealing container as defined in claim 1, further comprising:
   an opening unit which is contained by the plate-shaped member and is closed by the sealing film,
   a frame provided around the opening unit, and
   an operation film which is disposed at a position to face the sealing film to be parallel with each other when viewed from a side and covers the opening means in a state where the opening means can be operable,
   wherein the front chamber is a space surrounded by the sealing film, the frame, and the operation film.

10. The sealing container as defined in claim 9,
    wherein, under a plan view of the plate-shaped member, the opening means has a plate shape extending from a part of an inner peripheral surface of the frame toward an inside of the frame and has a blade on a tip side of the plate shape for forming a cut in the sealing film, and
    wherein the opening means is configured to be able to swing around a base end side thereof as a fulcrum.

11. The sealing container as defined in claim 10, wherein, under a plan view of the plate-shaped member, the blade is formed in a U-shape and is provided on an edge at the tip side of the opening means.

12. The sealing container as defined in claim 1, further comprising:
    a first bent portion for bending a first plate portion at which the bag-shaped member is attached to the plate-shaped member and a second plate portion adjacent to the first plate portion,
    a second bent portion which bends the plate-shaped member into the second plate portion and a cover plate portion adjacent to the second plate portion separately, and
    a storage means provided in the plate-shaped member for storing at least a part of the discharge pipe,
    wherein when the plate-shaped member is bent around the first bent portion, at least a part of the bag-shaped member is sandwiched between the first plate portion and the second plate portion to raise the pressure of the contents in the bag-shaped member, thereby discharging the contents, and
    wherein when the plate-shaped member is bent around the second bent portion, the discharge pipe is sandwiched between the second plate portion and the cover plate portion, whereby the discharge pipe is stored in the storage means.

13. The sealing container as defined in claim 12, wherein the protection means provided on the cover plate portion covers the operation unit when the plate-shaped member is bent around the second bent portion.

14. The sealing container as defined in claim 1, wherein the bag-shaped member is a discharge means which is capable of discharging the contents by being applied thereto the pressure at a timing different from a timing at which the opening means penetrates through the sealing film by the operation of the operation unit.

15. The sealing container as defined in claim 1,
    wherein the sealing container is a pre-filled syringe, and
    wherein the discharge pipe, under a plan view of the plate-shaped member, is an injection needle of the pre-filled syringe, and is provided at a position displaced to one side from a center position in a width direction of the plate-shaped member.

* * * * *